(12) United States Patent
Haynes et al.

(10) Patent No.: US 10,111,884 B2
(45) Date of Patent: *Oct. 30, 2018

(54) METHODS AND COMPOSITIONS FOR TREATING VIRAL INFECTIONS

(71) Applicants: THE HONG KONG UNIVERSITY OF SCIENCE AND TECHNOLOGY, Hong Kong (CN); HADASIT MEDICAL RSEARCH SERVICES AND DEVELOPMENT LTD., Jerusalem (IL)

(72) Inventors: Richard K. Haynes, Hong Kong (CN); Dana G. Wolf, Mevaseret Zion (IL)

(73) Assignees: Hadasit Medical Research Services and Development Ltd., Jerusalem (IL); The Hong Kong University of Science and Technology, Hong Kong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/361,150

(22) Filed: Nov. 25, 2016

(65) Prior Publication Data

US 2017/0071952 A1  Mar. 16, 2017

Related U.S. Application Data

(63) Continuation of application No. 14/394,973, filed as application No. PCT/IL2013/050335 on Apr. 17, 2013, now Pat. No. 9,616,067.

(60) Provisional application No. 61/625,701, filed on Apr. 18, 2012.

(51) Int. Cl.

| *A61K 31/54* | (2006.01) |
| *A61K 31/541* | (2006.01) |
| *A61K 31/357* | (2006.01) |
| *C07D 493/18* | (2006.01) |
| *A61K 45/06* | (2006.01) |
| *A61K 31/522* | (2006.01) |

(52) U.S. Cl.
CPC .......... *A61K 31/541* (2013.01); *A61K 31/357* (2013.01); *A61K 31/522* (2013.01); *A61K 45/06* (2013.01); *C07D 493/18* (2013.01)

(58) Field of Classification Search
CPC ....................................................... A61K 31/54
USPC ...................................................... 514/222.2
See application file for complete search history.

(56) References Cited

U.S. PATENT DOCUMENTS

| 4,920,147 | A | 4/1990 | McChesney et al. |
| 6,306,896 | B1 | 10/2001 | Scheiwe |
| 6,649,647 | B1 | 11/2003 | Haynes et al. |
| 6,984,640 | B1 * | 1/2006 | Haynes ................ A61K 31/355 |
| | | | 514/228.2 |
| 7,241,888 | B2 | 7/2007 | Hoelzer |
| 7,989,491 | B2 | 8/2011 | Schlegel et al. |
| 8,883,765 | B2 | 11/2014 | Arav-Boger et al. |
| 2005/0119232 | A1 | 6/2005 | Haynes |
| 2005/0282804 | A1 | 12/2005 | Hoelzer |
| 2007/0060499 | A1 | 3/2007 | Kosak |
| 2008/0161324 | A1 | 7/2008 | Johansen et al. |

FOREIGN PATENT DOCUMENTS

| CN | 1122806 A | 5/1996 |
| CN | 1317006 A | 10/2001 |
| CN | 1649874 A | 8/2005 |
| JP | 2002-520416 A | 7/2002 |
| JP | 2006-504787 A | 2/2006 |
| WO | 00/04026 A1 | 1/2000 |
| WO | 03076446 A1 | 9/2003 |
| WO | 2004/071506 A1 | 8/2004 |

OTHER PUBLICATIONS

Gravett et al., (2011) In vitro study of the anti-cancer effects of artemisone alone or in combination with other chemotherapeutic agents. Cancer Chemother Pharmacol 67: 569-77.
Krishna et al., (2008) Artemisinins: their growing importance in medicine. Trends Pharmacol Sci 29(10): 520-527.
Disbrow et al., (2005) Dihydroartemisinin is cytotoxic to papillomavirus-expressing epithelial cells in vitro and in vivo. Cancer Res 65(23): 10854-10861.
Janse et al., (1994) Comparison of in vivo and in vitro antimalarial activity of artemisinin, dihydroartemisinin and sodium artesunate in the Plasmodium berghei-rodent model. Int J Parasitol 24(4): 589-594.
Pittler and Ernst (1999) Artemether for severe malaria: a meta-analysis of randomized clinical trials. Clin Infect Dis 28: 597-601.
Boeckh et al., (2004) Optimization of quantitative detection of cytomegalovirus DNA in plasma by real-time PCR. J Clin Microbiol 42(3): 1142-8.
D'Alessandro et al., (2007) Differential effects on angiogenesis of two antimalarial compounds, dihydroartemisinin and artemisone: implications for embryotoxicity. Toxicology 241(1-2): 66-74.
Dunay et al., (2009) Artemisone and artemiside control acute and reactivated toxoplasmosis in a murine model. Antimicrob Agents Chemother 53(10): 4450-6.
Dziurzynski et al., (2012) Consensus on the role of human cytomegalovirus in glioblastoma, Neuro Oncol 14(3): 246-55.
Efferth et al., (2002) Antiviral activity of artesunate towards wild-type, recombinant, and ganciclovir-resistant human cytomegaloviruses, J Mol Med (Berl) 80(4): 233-42.
Efferth et al., (2008) The antiviral activities of artemisinin and artesunate. Clin Infect Dis 47(6): 804-11.

(Continued)

*Primary Examiner* — Jeffrey S Lundgren
*Assistant Examiner* — Stephanie K Springer
(74) *Attorney, Agent, or Firm* — Rothwell, Figg, Ernst & Manbeck, P.C.

(57) ABSTRACT

The present invention provides compositions and methods for treating, preventing, and inhibiting viral replication, viral infections and viral diseases and disorders, comprising the use of artemisinin derivatives having anti-viral activity.

23 Claims, 13 Drawing Sheets

(56) References Cited

OTHER PUBLICATIONS

Fox-Canale et al., (2007) Human cytomegalovirus and human immunodeficiency virus type-1 co-infection in human cervical tissue. Virology 369(1): 55-68.
Guo et al., (2012) Synthesis of artemiside and its effects in combination with conventional drugs against severe murine malaria. Antimicrob Agents Chemother 56(1): 163-73.
Haynes et al., (2006) Artemisone—a highly active antimalarial drug of the artemisinin class. Angew Chem Int Ed Engl 45(13): 2082-8.
Jacquemard et al., (2007) Maternal administration of valaciclovir in symptomatic intrauterine cytomegalovirus infection. BJOG 114(9): 1113-21.
Kaptein et al., (2006) The anti-malaria drug artesunate inhibits replication of cytomegalovirus in vitro and in vivo. Antiviral Res 69(2): 60-9.
Kolodkin-Gal et al., (2008) Herpes simplex virus type 1 preferentially targets human colon carcinoma: role of extracellular matrix. J Virol 82(2): 999-1010.
Nigro et al., (2005) Passive immunization during pregnancy for congenital cytomegalovirus infection. N Engl J Med 353(13): 1350-62.
Shapira et al., (2008) Artesunate as a potent antiviral agent in a patient with late drug-resistant cytomegalovirus infection after hematopoietic stem cell transplantation. Clin Infect Dis 46(9): 1455-7.
Vivas et al., (2007) Antimalarial efficacy and drug interactions of the novel semi-synthetic endoperoxide artemisone in vitro and in vivo. J Antimicrob Chemother 59(4): 658-65.
Weisblum et al., (2011) Modeling of human cytomegalovirus maternal-fetal transmission in a novel decidual organ culture. J Virol 85(24): 13204-13.
White et al., (2004) Small internal viruses with differential defects in viral deletions in the human cytomegalovirus IE2 gene result in nonviable recombinant gene expression. J Virol 78(4): 1817-30.
Wolf et al., (1995) Mutations in human cytomegalovirus UL97 gene confer clinical resistance to ganciclovir and can be J Clin Invest 95(1): 257-63.
Wolf et al., (2001) Distinct and separate roles for herpesvirus-conserved UL97 kinase in cytomegalovirus DNA synthesis and encapsidation. Proc Natl Aced Sci U S A 98(4): 1895-900.
Yang et al., (1995) Artemisinin derivatives with 12-aniline substitution: Synthesis and antimaterial activity. Bioorganic & Medicinal Chemistry Letters 5(16): 179-1794.
Haynes et al., (2007) The Fe2+-mediated decomposition, PfATP6 binding, and antimalarial activities of artemisone and other artemisinins: the unlikelihood of C-centered radicals as bioactive intermediates. ChemMedChem 2(10): 1480-97.
Office Action in corresponding Japanese Patent Application No. 2015-506363, dated Jun. 6, 2017, 2 pages.

* cited by examiner

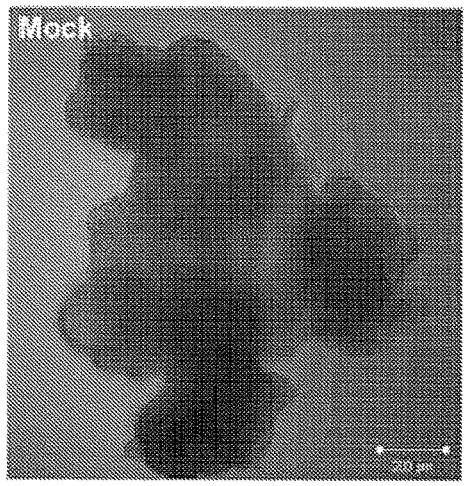
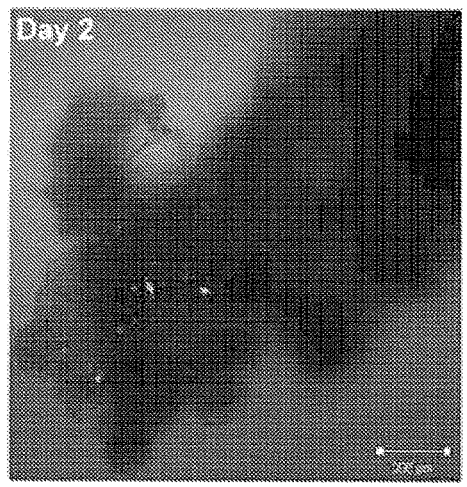
Figure 7A                Figure 7B
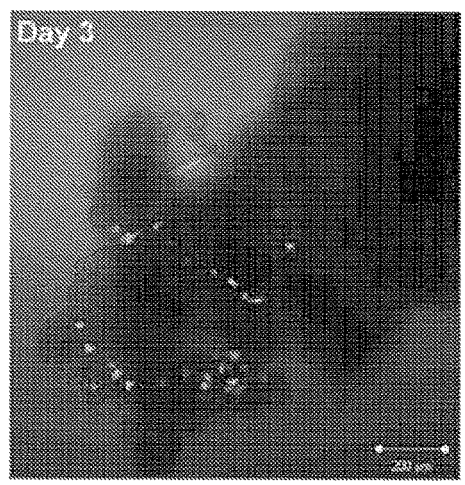
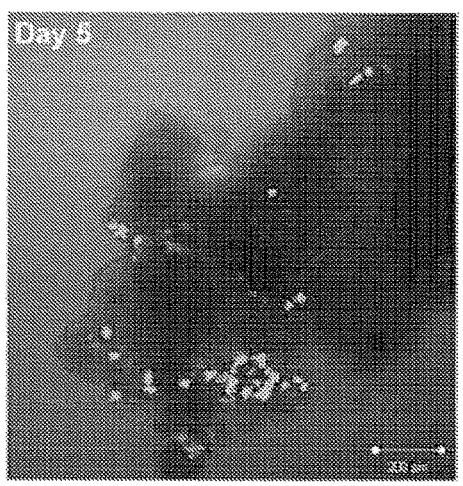
Figure 7C                Figure 7D

METHODS AND COMPOSITIONS FOR TREATING VIRAL INFECTIONS

This application is a continuation of U.S. Ser. No. 14/394,973 filed Oct. 16, 2014, which is a 35 U.S.C. § 371 national phase entry application from PCT/IL2013/050335, filed on Apr. 17, 2013, and designating the United States, which claims the benefit of U.S. Provisional Application No. 61/625,701 filed on Apr. 18, 2012, which are incorporated herein by reference in their entireties.

FIELD OF THE INVENTION

The present invention is directed to compositions and methods for inhibiting viral replication and treating viral infections, diseases and disorders, comprising the use of artemisinin derivatives having anti-viral activity.

BACKGROUND OF THE INVENTION

The compound artemisinin, also known as qinghaosu (III), is a tetracyclic 1,2,4-trioxane occurring in *Artemisia annua* and is described in U.S. Pat. No. 4,920,147 to McChesney et al. Artemisinin and its derivatives dihydroartemisinin (DHA) (IV), artemether (V) and artesunate (VI) (FIG. 1) have been used primarily for the treatment of malaria, as described in U.S. Pat. No. 6,306,896 to Scheiwe.

Chemical studies on artemisinin and its synthetic derivatives indicate that a cause of instability is the facile opening of the trioxane moiety in artemisinin, or in its derivative dihydroartemisinin. Ring opening provides the free hydroperoxide, which is susceptible to reduction. Removal of this group ensures destruction of drug activity with the reduction products being transformed into desoxo metabolites. In order to render ring-opening less facile, the oxygen atom at C-10 can be either removed to provide 10-deoxydihydroartemisinin, or replaced by other groups. This has provided the basis for the so-called "second generation" compounds which are generally 10-deoxy artemisinin derivatives. In addition, derivatives of artemisinin with a variety of substituents at C-9 have also been prepared.

Artemisinin derivatives in which the oxygen atom at C-10 is replaced by an amine group have been produced. For instance, Yang et al. (Biorg. Med. Chem. Lett., 1995, 5, 1791-1794) synthesized ten new artemisinin derivatives in which the oxygen atom at C-10 was replaced by —NHAr, where Ar represents a phenyl, 3-chlorophenyl, 4-chlorophenyl, 3-bromophenyl, 4-bromophenyl, 4-iodophenyl, 4-methylphenyl, 4-methoxyphenyl, 3-carboxylphenyl or 4-carboxylphenyl group. These compounds were tested for in vivo activity against the K173 strain of *Plasmodium berohei* and were found to be active.

U.S. Pat. No. 6,984,640 and United States patent application 2005/0119232 disclose certain C-10 substituted derivatives of artemisinin that are disclosed to be effective in the treatment of diseases caused by infection with a parasite of the genera *Plasmodium, Neospora* or *Eimeria*, especially *Plasmodium falciparum, Neospora caninum* and *Eimeria tenella*, which cause malaria, neosporosis and coccidiosis, respectively. The disclosed compounds are of the general formula I:

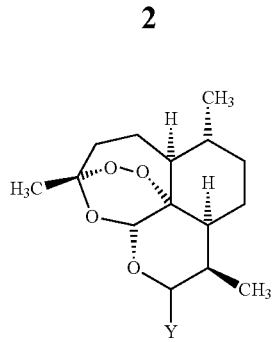

or a salt thereof, in which Y represents a halogen atom, an optionally substituted cycloalkyl, aryl, C-linked heteroaryl or heterocyclylalkyl group or a group —$NR^1R^2$; where $R^1$ represents a hydrogen atom or an optionally substituted alkyl, alkenyl or alkynyl group; $R^2$ represents an optionally substituted alkyl, alkenyl, alkynyl, cycloalkyl, aryl or aralkyl group; or $R^1$ and $R^2$ together with the interjacent nitrogen atom represent an optionally substituted heterocyclic group or an amino group derived from an optionally substituted amino acid ester; for use in the treatment and/or prophylaxis of a disease caused by infection with a parasite.

Artemisinin derivatives, artemisone and especially artemiside have been shown by Dunay et al. (Antimicrob Agents Chemother. 2009, 53(10), 4450-4456) to display enhanced inhibition of *Toxoplasma gondii*, and by Guo et al. (Antimicrob Agents Chemother. 2012, 56(1), 163-173) to have a pronounced effect on *Plasmodium falciparum*. Artemisone differs from currently used clinical artemisinins in that it does not elicit neurotoxicity in preclinical in vitro and in vivo screens. In a pilot tolerability test, treatment of male rats with artemisone at 50 mg/kg for 14 days had no effect as compared to controls. Studies involving proliferation of human endothelial cells and generation of new vessels, indicate that artemisone is significantly less anti-angiogenic than dihydroartemisinin, suggesting that it might be safer to use artemisone during pregnancy (D'Alessandro et al., Toxicology, 2007, 241, 66-74). Newer polar derivatives including the urea derivative RW177 have also been shown to have sub-nanomolar activity against the malarial parasite (see FIG. 1 for the structures of the derivatives).

U.S. Pat. No. 6,649,647 to one of the inventors of the present invention, discloses compounds containing a trioxane moiety, especially certain artemisinin derivatives, which have cytotoxic and anti-tumor activity and their use in the treatment of cancer. Some of these compounds comprise a ligand which is capable of binding to a nucleic acid and a group containing a trioxane moiety which is capable of acting as source of free radicals which are capable of chemically interacting with a nucleic acid. Processes for the preparation of such compounds and pharmaceutical compositions containing such compounds are also provided.

Viral infections account for a very large fraction of infectious disease mortality and morbidity worldwide. Cytomegalovirus (CMV), for example, a beta herpesvirus, is a major cause of morbidity and mortality in immunocompromised individuals including AIDS patients and recipients of hematopoietic stem cell transplantation (HSCT) or solid organ transplants. CMV is also the leading cause of congenital infection, affecting ~1% of live births, with resultant neurological damage and loss of hearing. Despite the considerable public health burden of congenital CMV, no established prenatal antiviral treatments are available.

In a transplantation setting, the widespread use of preventive antiviral therapy has reduced the occurrence of early CMV disease; however, the development of late disease is increasingly recognized. Preventive antiviral strategies include (a) preemptive therapy in patients who become positive for CMV antigen or CMV DNA in the blood after transplantation and (b) universal prophylaxis initiated in all at-risk patients at the time of engraftment and continued until 100 days after transplantation.

All currently available anti-CMV drugs, including ganciclovir, foscarnet and cidofovir, target the viral DNA polymerase. Although these drugs are effective, their use is limited by toxicity, low oral bioavailability, high cost, and teratogenicity. Additionally, prolonged or repeated antiviral treatment may lead to the development of drug resistance and occasionally cross-resistance to multiple drugs.

Artemisinin derivatives have been suggested for the treatment of viral infections. United States patent application 2008/0161324 suggests that artemisinins may be useful in combination with other agents in treating viral diseases. Artesunate has been shown to inhibit the replication of cytomegalovirus (CMV) (Efferth et al., J. Mol. Med., 2002, 80(4), 233-242) and has been used to treat CMV infection (Shapira et al., Clin. Infect. Dis., 2008, 46(9), 1455-1457).

None of the above references discloses or suggests use of 10-alkylamino artemisinin derivatives in treating viral infections or diseases resulting therefrom.

Thus, there is a clear need for effective and safe, anti-CMV drugs with high oral bioavailability. In addition, there remains a critical and unmet medical need for new therapeutic modes of treating viral infections.

SUMMARY OF THE INVENTION

The present invention provides compositions and methods for treating, attenuating, or inhibiting viral replication, viral infections, and viral diseases and disorders, comprising the use of artemisinin derivatives having anti-viral activity.

The present invention is based in part on the unexpected finding that several derivatives of artemisinin provide enhanced efficacy in treating CMV, either alone or in combination with other anti-viral drugs. Without being bound by any theory or mechanism of action, the artemisinin derivatives of the present invention are capable of inhibiting immediate early (IE) gene expression of human CMV virus.

In one embodiment, the present invention provides a method for treating a viral infection in a subject in need thereof, the method comprising the step of administering to the subject a pharmaceutical composition comprising a therapeutically effective amount of a compound having anti-viral activity of formula I:

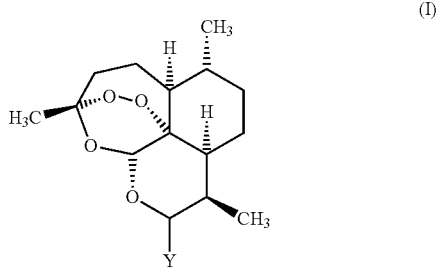

(I)

or a salt or a solvate thereof, wherein Y represents a group —NR$^1$R$^2$; wherein either
(i) R$^1$ represents a hydrogen atom or an optionally substituted alkyl, alkenyl or alkynyl group; and R$^2$ represents an optionally substituted alkyl, alkenyl, alkynyl, cycloalkyl, aryl or aralkyl group;
(ii) R$^1$ and R$^2$ together with the interjacent nitrogen atom represent a heterocyclic group or an amino group derived from an optionally substituted amino acid ester; or
(iii) R$^1$ represents a hydrogen atom or an optionally substituted alkyl, alkenyl, alkynyl, cycloalkyl, aryl or aralkyl group; and R$^2$ represents an —X(=Z)-A group, wherein
X represents a carbon atom, a sulfur atom, a sulfoxide group S=O, or a group PR$^3$, P—O—R$^3$ or P—N(R$^4$)—R$^3$, where R$^3$ and R$^4$ each independently represent a hydrogen atom or an optionally substituted alkyl, alkenyl, alkynyl, cycloalkyl, aryl or aralkyl group;
Z represents an oxygen atom, a sulfur atom or a group NR$^5$, where R$^5$ represents a hydrogen atom or an optionally substituted alkyl, alkenyl, alkynyl, cycloalkyl, aryl or aralkyl group; and
A represents a hydrogen atom or an optionally substituted alkyl, alkenyl, alkynyl, cycloalkyl, aryl or aralkyl group, or a group selected from N(R$^6$)$_2$, NHNH$_2$, NR$^6$NHR$^6$, NR$^6$N(R$^6$)$_2$, OR$^6$, SR$^6$, 10α-dihydroartemisinyl, OR$^7$ and NR$^6$R$^7$, where each R$^6$ independently represents a hydrogen atom or an optionally substituted alkyl, alkenyl, alkynyl, cycloalkyl, aryl or aralkyl group, and R$^7$ represents a bond attached as a substituent to R$^5$ or R$^1$ which together with the interjacent groups represent an optionally substituted heterocyclic group.

Each possibility represents a separate embodiment of the present invention.

In some embodiments, the present invention provides a pharmaceutical composition comprising a therapeutically effective amount of a compound having anti-viral activity of formula I as defined herein, for use in treating a viral infection.

In another embodiment, the present invention provides the use of a compound having anti-viral activity of formula I as defined herein, in the preparation of a medicament for treating a viral infection.

In one embodiment, the anti-viral activity of the compound of formula I as defined herein is an anti-cytomegalovirus activity. In specific embodiments, the compound having anti-cytomegalovirus activity of the present invention inhibits the expression of IE genes.

In certain embodiments, the viral infection is a herpesvirus infection. In additional embodiments, the herpesvirus is selected from herpes simplex virus (HSV) and Epstein-Barr virus (EBV). Each possibility represents a separate embodiment of the present invention. In other embodiments, the viral infection is a flavivirus infection. In specific embodiments, the flavivirus is Bovine Viral Diarrhea virus (BVDV). In further embodiments, the viral infection is hepatitis B virus (HBV) infection or hepatitis C virus (HCV) infection. Each possibility represents a separate embodiment of the present invention. In an exemplary embodiment, the viral infection is a cytomegalovirus infection, in particular human cytomegalovirus infection. In specific embodiments, the cytomegalovirus is a strain resistant to known anti-viral drugs. In other embodiments, the pharmaceutical composition of the present invention is effective in cases of congenital infection. In certain embodiments, the pharmaceutical composition of the present invention is effective in treating, attenuating or suppressing CMV infection in immunosuppressed patients including, in particular, transplantation recipients.

In some embodiments, the present invention provides a method for suppressing viral replication, the method comprising the step of administering to a subject in need thereof a pharmaceutical composition comprising a therapeutically effective amount of a compound having anti-viral activity of formula I:

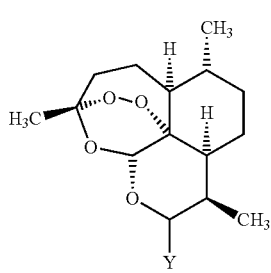

(I)

or a salt or a solvate thereof, wherein Y represents a group —NR$^1$R$^2$; wherein either
(i) R$^1$ represents a hydrogen atom or an optionally substituted alkyl, alkenyl or alkynyl group; and R$^2$ represents an optionally substituted alkyl, alkenyl, alkynyl, cycloalkyl, aryl or aralkyl group;
(ii) R$^1$ and R$^2$ together with the interjacent nitrogen atom represent a heterocyclic group or an amino group derived from an optionally substituted amino acid ester; or
(iii) R$^1$ represents a hydrogen atom or an optionally substituted alkyl, alkenyl, alkynyl, cycloalkyl, aryl or aralkyl group; and R$^2$ represents an —X(=Z)-A group, wherein
X represents a carbon atom, a sulfur atom, a sulfoxide group S=O or a group PR$^3$, P—O—R$^3$ or P—N(R$^4$)—R$^3$, where R$^3$ and R$^4$ each independently represent a hydrogen atom or an optionally substituted alkyl, alkenyl, alkynyl, cycloalkyl, aryl or aralkyl group;
Z represents an oxygen atom, a sulfur atom or a group NR$^5$, where R$^5$ represents a hydrogen atom or an optionally substituted alkyl, alkenyl, alkynyl, cycloalkyl, aryl or aralkyl group; and
A represents a hydrogen atom or an optionally substituted alkyl, alkenyl, alkynyl, cycloalkyl, aryl or aralkyl group, or a group selected from N(R$^6$)$_2$, NHNH$_2$, NR$^6$NHR$^6$, NR$^6$N(R$^6$)$_2$, OR$^6$, SR$^6$, 10α-dihydroartemisinyl, OR$^7$ and NR$^6$R$^7$, where each R$^6$ independently represents a hydrogen atom or an optionally substituted alkyl, alkenyl, alkynyl, cycloalkyl, aryl or aralkyl group, and R$^7$ represents a bond attached as a substituent to R$^5$ or R$^1$ which together with the interjacent groups represent an optionally substituted heterocyclic group.

Each possibility represents a separate embodiment of the present invention.

In particular embodiments, the method of suppressing viral replication is an ex-vivo method comprising suppressing viral replication in a cell or in an organ culture.

In other embodiments, the present invention provides a pharmaceutical composition comprising a therapeutically effective amount of a compound having anti-viral activity represented by the structure of formula I as defined herein, for use in suppressing viral replication.

In various embodiments, the present invention provides the use of a compound having anti-viral activity of formula I as defined herein, in the preparation of a medicament for suppressing viral replication.

In one embodiment, the anti-viral activity of the compound of formula I as defined herein is an anti-cytomegalovirus activity. In specific embodiments, the compound having anti-cytomegalovirus activity of the present invention inhibits the expression of IE genes.

In certain embodiments, the viral replication is a herpesvirus replication. In other embodiments, the viral replication is a flavivirus replication. In one embodiment, the viral replication is a cytomegalovirus replication, in particular human cytomegalovirus replication. In specific embodiments, the cytomegalovirus is a strain resistant to known anti-viral drugs.

In some embodiments, the compound having anti-viral activity of the present invention is represented by the structure of formula VII:

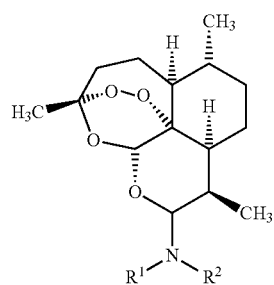

(VII)

wherein R$^1$ and R$^2$ together with the interjacent nitrogen atom represent a non-aromatic heterocyclic group.

In some embodiments, the compound having anti-viral activity of the present invention is 10α-(4'-(S,S-dioxothiomorpholin-1'-yl)-10-deoxo-10-dihydroartemisin, represented by the structure of formula VIII:

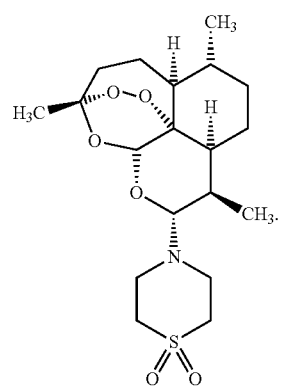

(VIII)

Artemisone

In further embodiments, the compound having anti-viral activity of the present invention is represented by the structure of formula IX:

(IX)

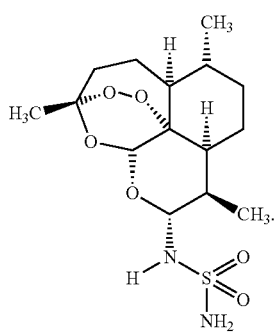

In other embodiments, the compound having anti-viral activity of the present invention is represented by the structure of formula X:

(X)

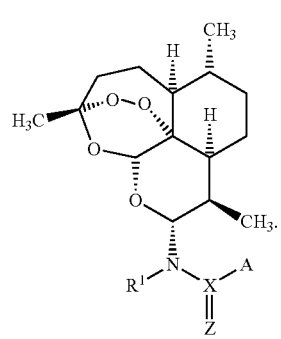

wherein $R^1$ represents a hydrogen atom or an optionally substituted alkyl, alkenyl, alkynyl, cycloalkyl, aryl or aralkyl group;

X represents a carbon atom, a sulfur atom, a sulfoxide group S=O or a group $PR^3$, P—O—$R^3$ or P—N($R^4$)—$R^3$ where $R^3$ and $R^4$ each independently represent a hydrogen atom or an optionally substituted alkyl, alkenyl, alkynyl, cycloalkyl, aryl or aralkyl group;

Z represents an oxygen atom, a sulfur atom or a group $NR^5$ where $R^5$ represents a hydrogen atom or an optionally substituted alkyl, alkenyl, alkynyl, cycloalkyl, aryl or aralkyl group; and A represents a hydrogen atom or an optionally substituted alkyl, alkenyl, alkynyl, cycloalkyl, aryl or aralkyl group, or a group selected from N($R^6$)$_2$, NHNH$_2$, $NR^6NHR^6$, $NR^6N(R^6)_2$, $OR^6$, $SR^6$, 10α-dihydroartemisinyl, $OR^7$ and $NR^6R^7$, where each $R^6$ independently represents a hydrogen atom or an optionally substituted alkyl, alkenyl, alkynyl, cycloalkyl, aryl or aralkyl group, and $R^7$ represents a bond attached as a substituent to $R^5$ or $R^1$ which together with the interjacent groups represent an optionally substituted heterocyclic group.

In further embodiments, the compound having anti-viral activity of the present invention is represented by the structure of formula X, wherein $R^1$ represents a hydrogen atom or an optionally substituted alkyl, alkenyl, alkynyl, cycloalkyl, aryl or aralkyl group; X represents a carbon atom, a sulfur atom, or a sulfoxide group S=O; Z represents an oxygen atom or a sulfur atom; and A represents a N($R^6$)$_2$, NHNH$_2$, $NR^6NHR^6$, or $NR^6N(R^6)_2$ group, where each $R^6$ independently represents a hydrogen atom or an optionally substituted alkyl, alkenyl, alkynyl, cycloalkyl, aryl or aralkyl group.

In other embodiments, the compound having anti-viral activity of the present invention has an aqueous solubility at pH 7.2 greater than 40 mg/L. In some embodiments, the compound having anti-viral activity of the present invention has a log P in the range of about 2.0-3.0. In particular embodiments, the compound having anti-viral activity of the present invention is incapable of being substantially converted in vivo to dihydroartemisinin.

In one embodiment, the pharmaceutical composition of the present invention further comprises a pharmaceutically acceptable carrier or excipient.

In various embodiments, the pharmaceutical composition of the present invention is suitable for administration via a route selected from the group consisting of oral, rectal, intramuscular, subcutaneous, intravenous, inrtaperitoneal, intranasal, intraarterial, intravesicle, intraocular, transdermal and topical. Each possibility represents a separate embodiment of the present invention.

According to some aspects and embodiments, the pharmaceutical composition of the present invention is in the form selected from the group consisting of tablets, pills, capsules, pellets, granules, powders, lozenges, sachets, cachets, elixirs, suspensions, dispersions, emulsions, solutions, syrups, aerosols, ointments, soft and hard gelatin capsules, suppositories, sterile injectable solutions, and sterile packaged powders. Each possibility represents a separate embodiment of the present invention.

In additional embodiments, the compound having anti-viral activity of the present invention is co-administered in combination with at least one other anti-viral drug. Exemplary and non-limiting embodiments include the co-administration of the compound having anti-viral activity of the present invention with an anti-viral drug selected from the group consisting of ganciclovir, valganciclovir, foscarnet, cidofovir, acyclovir and valacyclovir. Each possibility represents a separate embodiment of the present invention.

In particular embodiments, the compound having anti-viral activity of the present invention and the at least one other anti-viral drug together provide a therapeutic anti-viral effect which is at least additive.

In further embodiments, co-administration of the compound having anti-viral activity of the present invention and the at least one other anti-viral drug is performed in a regimen selected from a single combined composition, separate individual compositions administered substantially at the same time, and separate individual compositions administered under separate schedules. Each possibility represents a separate embodiment of the present invention.

In yet other embodiments, the present invention provides a method of treating a viral infection having oncomodulatory activity associated with the development of a tumor in a subject in need thereof, the method comprising the step of administering to the subject a pharmaceutical composition comprising a therapeutically effective amount of a compound having anti-viral activity of formula I as defined herein.

In additional embodiments, provided herein is a pharmaceutical composition comprising a therapeutically effective amount of a compound having anti-viral activity of formula I as defined herein, for use in treating a viral infection having oncomodulatory activity associated with the development of a tumor.

In further embodiments, the present invention provides the use of a compound having anti-viral activity of formula I as defined herein, in the preparation of a medicament for treating a viral infection having oncomodulatory activity associated with the development of a tumor.

In particular embodiments, the tumor is glioblastoma associated with cytomegalovirus infection. In another embodiment, the tumor is colon cancer or prostate cancer associated with cytomegalovirus infection. In other embodiments, the tumor is Burkitt's lymphoma associated with Epstein Barr Virus (EBV) infection. In another embodiment, the tumor is Hodgkin's lymphoma associated with EBV infection. In another embodiment, the tumor is post transplantation lympho-proliferative disorder (PTLD) associated with EBV infection. In yet another embodiment, the tumor is nasopharyngeal carcinoma associated with EBV infection. Each possibility represents a separate embodiment of the present invention.

Other objects, features and advantages of the present invention will become clear from the following description and drawings.

BRIEF DESCRIPTION OF THE DRAWINGS

FIG. 2A. Artemisone dose response curve, showing inhibition of CMV plaque formation following incubation with artemisone. Artemisone $IC_{50}$ value for this assay was 1.2 µM. FIG. 2B. Artemisone dose response curve, showing inhibition of CMV DNA accumulation following incubation with artemisone.

FIG. 3A. Artesunate dose response curve, showing inhibition of CMV plaque formation following incubation with artesunate. Artesunate $IC_{50}$ value for this assay was 15 µM. FIG. 3B. Artesunate dose response curve, showing inhibition of CMV DNA accumulation following incubation with artesunate.

FIG. 5A. HCMV IE antigen-positive cells in control untreated infected cells versus drug-treated infected cells. FIG. 5B. HCMV pp65 antigen-positive cells in control untreated infected cells versus drug-treated infected cells. Antigen-positive cells in control-untreated infected cells are presented as 100% for comparison.

FIGS. 6A-6B. H&E stained sections (5 micron) of uninfected decidual cultures prepared upon institution and at 8 days of culture. Arrows point to the surface epithelium of the decidua. FIGS. 6C-6D. Two different sections of cultures infected with HCMV strain PT30 ($10^4$ PFU/well), obtained at 6 dpi and subjected to H&E staining. Black arrows indicate infected cells with "owl's eye" inclusion bodies; white arrows indicate granular cytoplasmic inclusions; and black arrowheads indicate irregular hyperchromatic nuclei. FIGS. 6E-6F. Sections of cultures infected with HCMV strain PT30 ($10^4$ PFU/well), obtained at 6 dpi and subjected to immunohistochemical analysis for viral immediate-early (IE) (showing nuclear staining) and early-late (pp65) (showing mainly cytoplasmic staining) proteins.

FIGS. 7A-7D: HCMV infection kinetics in decidual cultures. Decidual organ cultures were infected with HCMV ($10^4$ PFU/well). Images of strain PT30-infected cells in live tissues as detected by confocal microscopy at: FIG. 7A. Mock-infected cells; FIG. 7B. Day 2; FIG. 7C. Day 3; and FIG. 7D. Day 5.

FIG. 11A. The indicated dilutions of HCMV HIG were incubated with $10^5$ PFU of HCMV strain TB40/E for 1 hour prior to infection, in order to examine viral neutralization. FIG. 11B. The indicated dilutions of HCMV HIG were added to the media of infected decidual cultures ($10^5$ PFU/well) following extensive washing of the infected tissues at 24 hours post adsorption. Viral DNA in decidual tissue lysates was quantitated at 8 dpi, and values were normalized by RNase P DNA copies. The results are expressed as a percentage of the amount of normalized HCMV DNA present in untreated cultures. Asterisks indicate significant differences between treated and untreated decidual cultures ($P<0.05$ by the two-tailed paired t test).

DETAILED DESCRIPTION OF THE INVENTION

Figure 1:
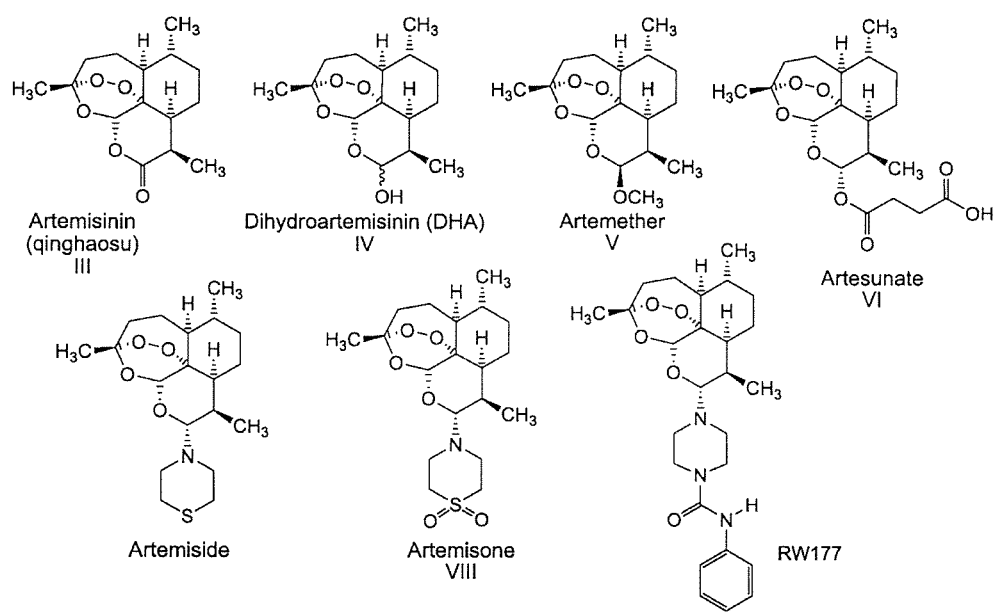
FIG. 1: Molecular structures of several artemisinin derivatives.

The present invention provides compositions and methods for treating, preventing, attenuating, and inhibiting viral replication, viral infections and viral diseases and disorders, comprising the use of artemisinin derivatives having antiviral activity, particularly anti-CMV activity.

HCMV gene expression occurs through a highly coordinated cascade of events involving three general classes of viral genes: immediate early (IE; mainly IE1 and IE2) genes, delayed-early genes, including mainly genes playing roles in viral DNA synthesis, and late viral genes-encoding the virion structural components. Although the replication cycle of HCMV is slow, requiring 48 to 72 hours to initiate the release of progeny, the expression of IE gene products starts immediately after viral entry and can be clearly detected at 24 hours post infection. Viral functions which are expressed early, play regulatory roles later in infection. The switch from early phase to late phase is delayed until 24 to 36 hours post infection, and occurs upon viral DNA synthesis, with maximal levels of late gene expression present at 72 to 96 hours post infection.

All currently approved anti-HCMV drugs, including ganciclovir, inhibit the viral DNA polymerase, and thus do not inhibit IE gene expression, but rather inhibit late gene expression.

The present invention is based in part on the unexpected finding that several 10-amino artemisinin derivatives are capable of blocking early steps as well as late steps of HCMV replication. Surprisingly, the compounds of the present invention were shown to effectively inhibit the expression of viral IE genes, which are the first genes to be expressed post infection. The ability to inhibit early gene expression provides a significant advantages over the hitherto known anti-viral agents which only affect late viral gene expression.

The present invention thus provides a method for treating a viral infection in a subject in need thereof, the method comprising the step of administering to the subject a therapeutically effective amount of a compound having anti-viral activity of formula I:

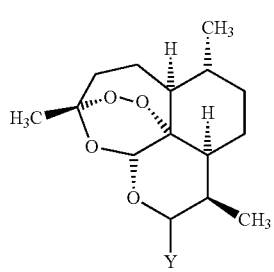

(I)

or a salt or a solvate thereof, wherein Y represents a group —NR$^1$R$^2$, thereby treating a viral infection in a subject.

In some aspects and embodiments, R$^1$ represents a hydrogen atom or an optionally substituted alkyl, alkenyl or alkynyl group; and R$^2$ represents an optionally substituted alkyl, alkenyl, alkynyl, cycloalkyl, aryl or aralkyl group.

In other aspects and embodiments, R$^1$ and R$^2$ together with the interjacent nitrogen atom represent a heterocyclic group or an amino group derived from an optionally substituted amino acid ester.

In yet other aspects and embodiments, R$^1$ represents a hydrogen atom or an optionally substituted alkyl, alkenyl, alkynyl, cycloalkyl, aryl or aralkyl group; and R$^2$ represents an —X(=Z)-A group, wherein
- X represents a carbon atom, a sulfur atom, a sulfoxide group S=O, or a group PR$^3$, P—O—R$^3$ or P—N(R$^4$)—R$^3$, where R$^3$ and R$^4$ each independently represent a hydrogen atom or an optionally substituted alkyl, alkenyl, alkynyl, cycloalkyl, aryl or aralkyl group;
- Z represents an oxygen atom, a sulfur atom or a group NR$^5$, where R$^5$ represents a hydrogen atom or an optionally substituted alkyl, alkenyl, alkynyl, cycloalkyl, aryl or aralkyl group; and
- A represents a hydrogen atom or an optionally substituted alkyl, alkenyl, alkynyl, cycloalkyl, aryl or aralkyl group, or a group selected from N(R$^6$)$_2$, NHNH$_2$, NR$^6$NHR$^6$, NR$^6$N(R$^6$)$_2$, OR$^6$, SR$^6$, 10α-dihydroartemisinyl, OR$^7$ and NR$^6$R$^7$, where each R$^6$ independently represents a hydrogen atom or an optionally substituted alkyl, alkenyl, alkynyl, cycloalkyl, aryl or aralkyl group, and R$^7$ represents a bond attached as a substituent to R$^5$ or R$^1$ which together with the interjacent groups represent an optionally substituted heterocyclic group.

Each possibility represents a separate embodiment of the present invention.

In various embodiments, the compound having anti-viral activity of the present invention is represented by any of the formulae VII, VIII, IX or X as defined herein below:

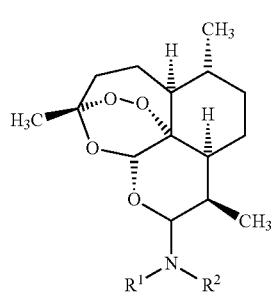

(VII)

wherein R$^1$ and R$^2$ together with the interjacent nitrogen atom represent a non-aromatic heterocyclic group;

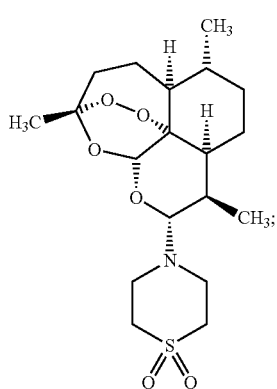

(VIII)

Artemisone

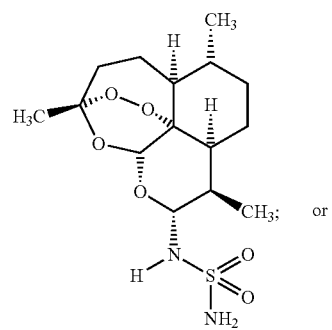

(IX)

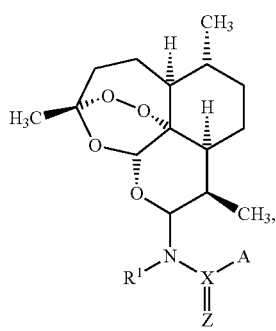

(X)

wherein R$^1$ represents a hydrogen atom or an optionally substituted alkyl, alkenyl, alkynyl, cycloalkyl, aryl or aralkyl group;

X represents a carbon atom, a sulfur atom, a sulfoxide group S=O or a group $PR^3$, P—O—$R^3$ or P—N($R^4$)—$R^3$ where $R^3$ and $R^4$ each independently represent a hydrogen atom or an optionally substituted alkyl, alkenyl, alkynyl, cycloalkyl, aryl or aralkyl group;

Z represents an oxygen atom, a sulfur atom or a group $NR^5$ where $R^5$ represents a hydrogen atom or an optionally substituted alkyl, alkenyl, alkynyl, cycloalkyl, aryl or aralkyl group; and A represents a hydrogen atom or an optionally substituted alkyl, alkenyl, alkynyl, cycloalkyl, aryl or aralkyl group, or a group $N(R^6)_2$, $NHNH_2$, $NR^6NHR^6$ or $NR^6N(R^6)_2$, or a group $OR^6$ or $SR^6$ where each $R^6$ independently represents a hydrogen atom or an optionally substituted alkyl, alkenyl, alkynyl, cycloalkyl, aryl or aralkyl group, or a 10α-dihydroartemisinyl group, or A represents a group $OR^7$ or $NR^6R^7$, where $R^6$ represents a group as defined above and $R^7$ represents a bond attached as a substituent to $R^5$ together with the interjacent group —X(=Z)— forming an optionally substituted heterocyclic group where Z represents a group $NR^5$, or $R^7$ represents a bond attached as a substituent to $R^1$ together with the interjacent group —N—X(=Z)— forming an optionally substituted heterocyclic group.

Each possibility represents a separate embodiment of the present invention.

Disclosed herein is the use of the compound having anti-viral activity of any of formulae I, VII, VIII, IX or X for the preparation of a medicament for treating a viral infection. The present invention further provides the compound having anti-viral activity of any of formulae I, VII, VIII, IX or X or a pharmaceutical composition comprising same for use in treating a viral infection.

The term "treating" as used herein includes the diminishment, alleviation, or amelioration of at least one symptom associated or caused by the state, disorder or disease being treated. In some embodiments, the term "treating" as used herein refers to the inhibition of viral replication with reduction of viral load. Accordingly, the term "treating" further encompasses prophylaxis or preemptive treatment, namely the prevention of infection and disease in yet uninfected or infected asymptomatic patients. In one embodiment, the treatment is effected ex-vivo. The term "a therapeutically effective amount" as used herein refers to an amount of an agent which is effective, upon single or multiple dose administration to the subject in providing a therapeutic benefit to the subject. In one embodiment, the therapeutic benefit is inhibiting virus activity. As used herein, the term "administering" refers to bringing in contact with the compound or composition of the present invention. Administration can be accomplished to cells or tissue cultures, or to living organisms, for example mammals, in particular humans.

Within the scope of the present invention is a method for suppressing viral replication, the method comprising the step of administering a compound having anti-viral activity of any of formulae I, VII, VIII, IX or X or a composition comprising said compound and a pharmaceutically acceptable carrier or excipient. Additional embodiments provide the use of a compound having anti-viral activity of any of formulae I, VII, VIII, IX or X for the preparation of a medicament for suppressing viral replication. According to some aspects and embodiments, the present invention provides a compound having anti-viral activity of any of formulae I, VII, VIII, IX or X or a pharmaceutical composition comprising same for use in suppressing viral replication. In a particular embodiment, the methods and use provided herein are directed to suppressing viral replication in a cell or in an organ culture comprising the step of contacting the cell or the organ culture with a compound having anti-viral activity of any of formulae I, VII, VIII, IX or X or a composition comprising said compound and a pharmaceutically acceptable carrier or excipient.

The alkyl, alkenyl or alkynyl group represented by $R^1$ in formula I is, in some embodiments, substituted. In another embodiment, the alkyl, alkenyl or alkynyl group is unsubstituted. Each possibility represents a separate embodiment of the present invention.

The alkyl, alkenyl, alkynyl, cycloalkyl, aryl or aralkyl group represented by $R^1$ or $R^2$ in formula I; or represented by $R^1$, A or Z in formula X is, in some embodiments, substituted. In another embodiment, the alkyl, alkenyl, alkynyl, cycloalkyl, aryl or aralkyl group is unsubstituted. Each possibility represents a separate embodiment of the present invention.

As provided herein, 10-amino artemisinin derivatives exhibit extremely high anti-viral efficacy. This property, combined with their excellent safety and tolerability profiles, renders them an attractive choice for treatment of viral infections and diseases and disorders engendered thereby.

In another embodiment, Y of formula I represents a group —$NR^1R^2$, wherein $R^1$ and $R^2$ together with the interjacent nitrogen atom form a non-aromatic heterocyclic group. In another embodiment, the non-aromatic heterocyclic group is substituted. In another embodiment, the non-aromatic heterocyclic group is unsubstituted. Each possibility represents a separate embodiment of the present invention.

In another embodiment, the non-aromatic heterocyclic group is substituted with a polar moiety.

In another embodiment, the non-aromatic heterocyclic group is piperazine. In certain embodiments, the non-aromatic heterocyclic group is morpholine. In another embodiment, the non-aromatic heterocyclic group is thiomorpholine. In another embodiment, the non-aromatic heterocyclic group is morpholino-sulfone. In another embodiment, the non-aromatic heterocyclic group is selected from the group consisting of piperazinyl, morpholinyl, thiomorpholinyl, and mopholinosulphonyl. Each possibility represents a separate embodiment of the present invention.

In particular embodiments, the compound of the present invention is artemisone (formula VIII). Artemisone, also known as "10α-(4'-(S,S-dioxothiomorpholin-1'-yl)-10-deoxo-10-dihydroartemisin" and "BAY 44-9585," is available from Bayer AG (Germany).

In another embodiment, the compound of the present invention is 10α-(4'-benzylpiperazin-1'-yl)-10-deoxo-10-dihydroartemisinin.

In another embodiment, the compound of the present invention is 10α-(morpholino) 10-deoxo-10-dihydroartemisinin.

In another embodiment, the compound of the present invention is 10α-(1-(2-pyrimidyl)-piperazino)-10-deoxo-10-dihydroartemisinin.

In another embodiment, the compound of the present invention is 10α-(sulfamino)-dihydroartemisinin.

In some embodiments, the compound of the present invention is represented by the structure of formula X, wherein $R^1$ represents a hydrogen atom or an optionally substituted alkyl, alkenyl, alkynyl, cycloalkyl, aryl or aralkyl group; X represents a carbon atom, a sulfur atom, or a sulfoxide group S=O; Z represents an oxygen atom or a sulfur atom; and A represents a $N(R^6)_2$, $NHNH_2$, $NR^6NHR^6$, or $NR^6N(R^6)_2$ group, where each $R^6$ independently represents a hydrogen atom or an optionally substituted alkyl, alkenyl, alkynyl, cycloalkyl, aryl or aralkyl group.

In particular embodiments, the compound of the present invention is represented by the structure of formula I, wherein Y represents a —$NR^1R^2$ group, where $R^1$ represents a hydrogen atom and $R^2$ represents an —X(=Z)-A group in which, X represents a sulfoxide group S=O, Z represents an oxygen atom, and A represents a $NH_2$ group.

Any alkyl, alkenyl or alkynyl group, unless otherwise specified, may be linear or branched and may contain up to 12, up to 6, or up to 4 carbon atoms. Non-limiting examples of alkyl groups are methyl, ethyl, propyl and butyl. In some embodiments, the alkenyl or alkynyl group is not an alk-1-enyl or alk-1-ynyl group. In accordance with these embodiments, there is at least one methylene group —$CH_2$— or similar $sp^3$-hybridised center between a carbon atom forming part of the double or triple C—C bond and the nitrogen atom to which the group is attached. Non-limiting examples of alkenyl and alkynyl groups include propenyl, butenyl, propynyl and butynyl groups. When an alkyl moiety forms part of another group, for example the alkyl moiety of an aralkyl group, it may contain up to 6, or up to 4 carbon atoms. Exemplary alkyl moieties are methyl and ethyl.

An aryl group may be any aromatic hydrocarbon group and may contain from 6 to 24, preferably 6 to 18, more preferably 6 to 16, and especially 6 to 14 carbon atoms. Non-limiting examples of aryl groups include phenyl, naphthyl, anthryl, phenanthryl and pyryl groups, especially a phenyl or napthyl, and particularly a phenyl group. When an aryl moiety forms part of another group, for example the aryl moiety of an aralkyl group, it may be a phenyl, naphthyl, anthryl, phenanthryl or pyryl, especially phenyl or naphthyl, and particularly a phenyl moiety.

An aralkyl group may be any alkyl group substituted by an aryl group. Suitable aralkyl group contains from 7 to 30, particularly 7 to 24 and especially 7 to 18 carbon atoms. Non-limiting examples of aralkyl groups include benzyl, naphthylmethyl, anthrylmethyl, phenanthrylmethyl and pyrylmethyl groups. An exemplary aralkyl group is a benzyl group.

A cycloalkyl group may be any saturated cyclic hydrocarbon group and may contain from 3 to 12, for example 3 to 8, and especially 3 to 6 carbon atoms. Non-limiting examples of cycloalkyl groups are cyclopropyl, cyclopentyl and cyclohexyl groups.

A heteroaryl group may be any aromatic monocyclic or polycyclic ring system which contains at least one heteroatom. Typically, a heteroaryl group is a 5-18-membered, particularly a 5-14-membered, and especially a 5-10-membered aromatic ring system containing at least one heteroatom selected from an oxygen, a sulfur and a nitrogen atom. Non-limiting heteroaryl groups include pyridyl, pyrylium, thiopyrylium, pyrrolyl, furyl, thienyl, indolinyl, isoindolinyl, indolizinyl, imidazolyl, pyridonyl, pyronyl, pyrimidinyl, pyrazinyl, oxazolyl, thiazolyl, purinyl, quinolinyl, isoquinolinyl, quinoxalinyl, pyridazinyl, benzofuranyl, benzoxazolyl and acridinyl groups. A C-linked heteroaryl group is a heteroaryl group as defined above which is linked to the tetracyclic 1,2,4-trioxane moiety of a compound of the present invention via a carbon atom in the heteroaromatic ring system.

A heterocyclic group may be any monocyclic or polycyclic ring system which contains at least one heteroatom and may be unsaturated or partially or fully saturated. The term "heterocyclic" thus includes heteroaryl groups as defined above as well as non-aromatic heterocyclic groups. Typically, a heterocyclic group is a 3-18-membered, particularly a 3-14-membered, especially a 5-10-membered ring system containing at least one heteroatom selected from an oxygen, a sulfur and a nitrogen atom. Non-limiting examples of heterocyclic groups include the specific heteroaryl groups named above as well as pyranyl, piperidinyl, pyrrolidinyl, dioxanyl, piperazinyl, morpholinyl, thiomorpholinyl, morpholinosulphonyl, tetrahydroisoquinolinyl and tetrahydrofuranyl groups.

A heterocyclylalkyl group may be any alkyl group substituted by a heterocyclic group. Typically, the heterocyclic moiety is a 3-18-membered, particularly a 3-14-membered, and especially a 5-10-membered heterocyclic group as defined above and the alkyl moiety is a $C_{1-6}$ alkyl, or $C_{1-4}$ alkyl, for example a methyl group.

An amino acid may be any α-amino acid, such as glycine, alanine, valine, leucine, isoleucine, serine, threonine, cysteine, cystine, methionine, aspartic acid, glutamic acid, asparagine, glutamine, lysine, hydroxylysine, arginine, histidine, phenylalanine, tyrosine, tryptophan, proline, hydroxyproline or phenylglycine, and includes both D- and L-configurations. An amino acid ester may be any ester of such an amino acid, for example alkyl esters such as $C_{1-4}$ alkyl esters.

When any of the foregoing substituents are designated as being optionally substituted, the substituent groups which are optionally present may be any one or more of those customarily employed in the development of pharmaceutical compounds and/or the modification of such compounds to influence their structure/activity, stability, bioavailability or other property. Specific examples of such substituents include, for example, halogen atoms, nitro, cyano, hydroxyl, cycloalkyl, alkyl, alkenyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, alkylsulphonato, arylsulphinyl, arylsulphonyl, arylsulphonato, carbamoyl, alkylamido, aryl, aralkyl, optionally substituted aryl, heterocyclic and alkyl- or aryl-substituted heterocyclic groups. When any of the foregoing substituents represents or contains an alkyl or alkenyl substituent group, this may be linear or branched and may contain up to 12, up to 6, and especially up to 4 carbon atoms. A cycloalkyl group may contain from 3 to 8, for example from 3 to 6 carbon atoms. An aryl group or moiety may contain from 6 to 10 carbon atoms, for example phenyl groups. A heterocyclic group or moiety may be a 5-10-membered ring system as defined above. A halogen atom may be a fluorine, chlorine, bromine or iodine atom and any group which contains a halo moiety, such as a haloalkyl group containing any one or more of these halogen atoms.

In one aspect, Y may represent a halogen atom, particularly a fluorine or bromine, and especially a fluorine atom.

In another aspect, Y may represent a $C_{3-8}$ cycloalkyl group, a $C_{6-18}$ aryl group, a 5-10-membered C-linked heteroaryl group or a 5-10-membered heterocyclyl-$C_{1-6}$ alkyl group, each group being optionally substituted by one or more substituents selected from the group consisting of halogen atoms, hydroxyl, $C_{1-4}$ alkyl, $C_{2-4}$ alkenyl, $C_{1-4}$ haloalkyl, $C_{1-4}$ alkoxy, amino, $C_{1-4}$ alkylamino, di($C_{1-4}$ alkyl)amino, carboxyl, $C_{6-10}$ aryl, 5-10-membered heterocyclic and $C_{1-4}$ alkyl- or phenyl-substituted 5-10-membered heterocyclic groups. Each possibility represents a separate embodiment of the present invention. According to some aspects and embodiments, Y may represent a $C_{6-18}$ aryl group optionally substituted by one or more substituents selected from the group consisting of halogen atoms, hydroxyl, $C_{1-4}$ alkyl, $C_{2-4}$ alkenyl, $C_{1-4}$ haloalkyl, $C_{1-4}$ alkoxy, $C_{1-4}$ haloalkoxy, amino, $C_{1-4}$ alkylamino, di($C_{1-4}$ alkyl)amino and carboxyl groups. Each possibility represents a separate embodiment of the present invention. In particular, Y may represent a phenyl, naphthyl, anthryl or phenanthryl group, each group being optionally substituted by one or more substituents selected from the group consisting of halogen atoms and hydroxyl, methyl, vinyl, $C_{1-4}$ alkoxy and carboxyl groups. Each possibility represents a separate embodiment of the present invention.

In another sub-group of compounds, Y may represent a phenyl, fluorophenyl, chlorophenyl, bromophenyl, triethylphenyl, vinylphenyl, methoxyphenyl, dimethoxyphenyl, trimethoxyphenyl, carboxylphenyl, naphthyl, hydroxynaphthyl, methoxynaphthyl, anthryl or phenanthryl group. Each possibility represents a separate embodiment of the present invention. Compounds in which Y may represent a phenyl or trimethoxyphenyl group are also included within the scope of the present invention.

In a further aspect, Y may represent a group —$NR^1R^2$ where $R^1$ represents a hydrogen atom or a $C_{1-6}$ alkyl group and $R^2$ represents a $C_{1-6}$ alkyl, $C_{3-4}$ cycloalkyl, $C_{6-10}$ aryl or $C_{7-16}$ aralkyl group, or $R^1$ and $R^2$ together with the interjacent nitrogen atom represent a 5-10-membered heterocyclic group or an amino group derived from a $C_{1-6}$ alkyl ester of an amino acid, each group being optionally substituted by one or more substituents selected from the group consisting of halogen atoms, $C_{1-4}$ alkyl, $C_{1-4}$ haloalkyl, $C_{1-6}$ alkoxycarbonyl, phenyl, halophenyl, $C_{3-4}$ alkylphenyl, $C_{1-4}$ haloalkylphenyl, $C_{1-4}$ alkoxyphenyl, benzyl, pyridyl and pyrimidinyl groups. Each possibility represents a separate embodiment of the present invention. In particular, Y may represent a group —$NR^1R^2$ where $R^1$ represents a hydrogen atom or a $C_{1-4}$ alkyl group and $R^2$ represents a $C_{1-4}$ alkyl, $C_{3-6}$ cycloalkyl, phenyl or benzyl group, or $R^1$ and $R^2$ together with the interjacent nitrogen atom represent a 6-10-membered heterocyclic group or an amino group derived from a $C_{1-4}$ alkyl ester of an amino acid, each group being optionally substituted by one or more substituents selected from the group consisting of halogen atoms, $C_{1-4}$ haloalkyl, $C_{1-4}$ alkoxycarbonyl, phenyl, halophenyl, $C_{1-4}$ alkylphenyl, $C_{1-4}$ haloalkylphenyl, $C_{1-4}$ alkoxyphenyl, benzyl, pyridyl and pyrimidinyl groups. Each possibility represents a separate embodiment of the present invention.

In another sub-group of these compounds, Y represents a propylamino, cyclopentylamino, cyclohexylamino, phenylamino, fluorophenylamino, chlorophenylamino, bromophenylamino, iodophenylamino, methoxycarbonylphenylamino, biphenylamino, benzylamino, fluorobenzylamino, bis(trifluoromethyl)-benzylamino, phenylethylamine, phenylmethoxycarbonyl methylamino, diethylamino, morpholinyl, thiomorpholinyl, morpholinosulphonyl, indolinyl, tetrahydroisoquinolinyl, phenylpiperazinyl, fluorophenylpiperazinyl, chlorophenylpiperazinyl, methylphenylpiperazinyl, trifluoromethylphenylpiperazinyl, methoxyphenylpiperazinyl, benzylpiperazinyl, pyridylpiperazinyl and pyrimidinylpiperazinyl group. Exemplary compounds include, but are not limited to, compounds in which Y represents a propylamino, phenylamino, bromophenylamino, iodophenylamino, biphenylamino, benzylamino, bis(trifluoromethyl)benzylamino, phenylethylamino, phenyl-methoxycarbonylmethyl amino or morpholinyl group. Each possibility represents a separate embodiment of the present invention.

In another embodiment, a method of the present invention utilizes a compound of the general formula I as defined above, with the proviso that, when Y is a group —$NR^1R^2$ and $R^2$ represents a phenyl, 3-chlorophenyl, 4-chlorophenyl, 3-bromophenyl, 4-bromophenyl, 4-iodophenyl, 4-methylphenyl, 4-methoxyphenyl, 3-carboxylphenyl or 4-carboxylphenyl group, then $R^1$ is an optionally substituted alkyl group.

One or more of the compounds of the invention, may be present as a salt. Suitable salts of artemisinin derivatives of the present invention include both basic and acid addition salts. In particular embodiments, acid addition salts, which can be formed by the reaction of a suitable compound of formulae I, VII, VIII, IX or X with a suitable acid, such as an organic acid or a mineral acid are encompassed by the present invention. Acid addition salts formed by the reaction with a mineral acid are suitable according to the principles of the present invention, especially salts formed by reaction with hydrochloric or hydrobromic acid. Compounds of formula I in which Y represents a group —$NR^1R^2$, wherein $R^1$ and $R^2$ are as defined above, are particularly suitable for the formation of such acid addition salts.

It should also be appreciated that the compounds of general formulae I, VII, VIII, IX or X are capable of existing as different geometric and optical isomers. The present invention thus includes both the individual isomers and mixtures of such isomers. The present invention also includes solvates of the compounds of the present invention and solvates of salts as described herein. "Solvate" means a physical association of a compound of the invention with one or more solvent molecules. This physical association involves varying degrees of ionic and covalent bonding, including hydrogen bonding. "Solvate" encompasses both solution-phase and isolatable solvates. Non-limiting examples of suitable solvates include ethanolates, methanolates and the like. "Hydrate" is a solvate wherein the solvent molecule is water.

The present invention also includes polymorphs of the compounds of the present invention and salts thereof. The term "polymorph" refers to a particular crystalline or amorphous state of a substance, which can be characterized by particular physical properties such as X-ray diffraction, IR or Raman spectra, melting point, and the like.

Methods for producing the compounds of the present invention are known in the art, and are described inter alia in U.S. Pat. No. 6,984,640 and United States patent application 2005/0119232, the contents of which are incorporated herein by reference.

In another embodiment, the compounds of the present invention exhibits an aqueous solubility at pH 7.2 greater than 40 mg/L. In other embodiments, the aqueous solubility is within the range of about 40-1000 mg/L. In yet other embodiments, the aqueous solubility is within the range of about 30-1000 mg/L. In further embodiments, the aqueous solubility is within the range of about 50-1000 mg/L. In additional embodiments, the aqueous solubility is within the range of about 60-1000 mg/L. In various embodiments, the aqueous solubility is within the range of about 40-800 mg/L. In certain embodiments, the aqueous solubility is within the range of about 40-600 mg/L. In some embodiments, the aqueous solubility is within the range of about 40-400 mg/L. In other embodiments, the aqueous solubility is within the range of about 40-2000 mg/L. In particular embodiments, the aqueous solubility is within the range of about 20-1000 mg/L. In yet another embodiment, the aqueous solubility is within the range of about 20-800 mg/L. Each possibility represents a separate embodiment of the present invention.

According to some aspects and embodiments, the compounds of the present invention exhibit a log P between about 2.0-3.0, inclusive. log P, as used herein, refers to the octanol-water partition coefficient. In certain embodiments, the log P is between about 2.1-2.9, inclusive. In another embodiment, the log P is between about 2.2-2.8, inclusive. In yet another embodiment, the log P is between about 2.3-2.7, inclusive. In additional embodiments, the log P is between about 2.1-3.0, inclusive. In further embodiments, the log P is between about 2.2-3.0, inclusive. In other embodiments, the log P is between about 2.0-2.9, inclusive. In certain embodiments, the log P is between about 2.0-2.8, inclusive. In particular embodiments, the log P is between about 2.4-2.8, inclusive. Each possibility represents a separate embodiment of the present invention.

According to some aspects and embodiments, the compounds of the present invention are not capable of being substantially converted in vivo to dihydroartemisinin. It is contemplated that this property enhances the safety of these compounds by reducing the already low likelihood of neurotoxicity. "Substantially converted" as used herein refers to in vivo conversion to dihydroartemisinin to an extent detectable by standard metabolic fate assays. Metabolic fate assays are well known in the art, and include, for example, administration of a compound of the present invention labeled with $^{14}C$ or $^{2}H$ to human liver microsomes, followed by identification of metabolites produced by 1D and 2D nuclear magnetic resonance (NMR) (Haynes et al., Angew. Chem. Int. Ed., 2006, 45, 2082-2088). In another embodiment, any other metabolic fate assay known in the art is utilized. Each possibility represents a separate embodiment of the present invention.

In certain embodiments, the viral infection which is treated, inhibited, attenuated or suppressed by a method of the present invention is a herpesvirus infection. In another embodiment, the herpesvirus is selected from the group consisting of herpes simplex virus (HSV) type 1, HSV type 2, varicella-zoster virus, cytomegalovirus, Epstein-Barr virus (EBV), human herpesvirus 6, human herpesvirus 7, and human herpesvirus 8 (Kaposi's Sarcoma associated Herpes Virus). Each possibility represents a separate embodiment of the present invention. Human herpesvirus 6 as used herein encompasses both variants A and B. Each possibility represents a separate embodiment of the present invention. In another embodiment, the viral infection is an alpha herpesvirus infection. In certain embodiments, the viral infection is a beta herpesvirus infection. In another embodiment, the viral infection is a gamma herpesvirus infection. In yet another embodiment, the viral infection is a cytomegalovirus infection. In an exemplary embodiment, the viral infection is a human cytomegalovirus infection. In another embodiment, the viral infection is a flavivirus infection. In specific embodiments, the flavivirus infection is Bovine Viral Diarrhea virus (BVDV) infection. In other embodiments, the viral infection is hepatitis B virus (HBV) infection or hepatitis C virus (HCV) infection. Each possibility represents a separate embodiment of the present invention. In further embodiments, the viral infection is any other type of viral infection known in the art.

It will be understood by those skilled in the art that the compositions and methods of the present invention have utility for treating not only viral infections themselves, but also diseases and disorders engendered by viral infections. Thus, for example, the present invention provides a method of treating a viral infection having oncomodulatory activity on a tumor in a subject in need thereof comprising administering to said subject a therapeutically effective amount of a compound having anti-viral activity of any of formulae I, VII, VIII, IX or X as defined herein or a pharmaceutical composition comprising said compound and a pharmaceutically acceptable carrier or excipient. For example, there is some evidence that HCMV could modulate the malignant phenotype in glioblastomas, where HCMV sequences and viral gene expression exist in most, if not all, malignant gliomas (Dziurzynski et al., 2012, Neuro-Oncology, doi: 10.1093/neuonc/nor227). Thus, according to some aspects and embodiments, the present invention provides a method of treating a viral infection having oncomodulatory activity on a tumor, in particular glioblastoma associated with cytomegalovirus in a subject in need thereof, the method comprising administering to said subject a therapeutically effective amount of a compound having anti-viral activity of any of formulae I, VII, VIII, IX or X as defined herein or a pharmaceutical composition comprising said compound and a pharmaceutically acceptable carrier or excipient. The method of the present invention encompasses the direct targeting of cytomegalovirus in glioblastoma patients or alternatively modulating the transformed phenotype in glioblastoma patients. Each possibility represents a separate embodiment of the present invention. In some embodiments, the compounds of the present invention prevent or decrease the likelihood of developing glioblastoma in subjects who are afflicted with cytomegalovirus.

Further encompassed by the present invention is the treatment of CMV infection, wherein the CMV is associated with a tumor such as, but not limited to, colon cancer, prostate cancer and the like, and the treatment of EBV, wherein the EBV is associated with a tumor such as, but not limited to, Burkitt's lymphoma, Hodgkin's lymphoma, post transplantation lympho-proliferative disorder (PTLD), and nasopharyngeal carcinoma. Each possibility represents a separate embodiment of the present invention.

It will also be understood by those skilled in the art that the compounds of the present invention are useful for prevention, attenuation or treatment and control of viral infection and disease in humans and animals. In some embodiments, the treatment is effective in cases of congenital infection. In additional embodiments, the treatment is effective in cases of CMV infection in immunosuppressed patients including transplantation recipients. In particular embodiments the treatment is effective ex-vivo. Within the scope of the present invention is the treatment of newborns that are infected with HCMV, pregnant women who are infected with HCMV, and transplantation recipients. Each possibility represents a separate embodiment of the present invention.

According to certain aspects and embodiments, the present invention provides the combination therapy comprising the compounds of the present invention and at least one other antiviral drug. In one embodiment, the compound of the present invention is used in combination with a viral DNA polymerase inhibitor. In another embodiment, the viral DNA polymerase inhibitor is selected from the group consisting of ganciclovir, foscarnet and cidofovir. Each possibility represents a separate embodiment of the present invention. In yet another embodiment, the viral DNA polymerase inhibitor is any other viral DNA polymerase inhibitor known to those of skill in the art. In certain embodiments, a compound of the present invention is used in combination with an anti-viral drug including, but not limited to, ganciclovir, valganciclovir, foscarnet, cidofovir, acyclovir, valacyclovir, and any other anti-viral drug known in the art. Each possibility represents a separate embodiment of the present invention. In additional embodiments, a compound of the present invention is used in combination with any one of maribavir, letermovir (also known as AIC246), CMX-001, CMV hyperimmune globulins and CMV monoclonal antibodies. Each possibility represents a separate embodiment of the present invention.

Should the compositions of the present invention be administered as a combination therapy with additional therapeutic agents (e.g. other anti-viral agents), the treatment may take place sequentially in any order, simultaneously or a combination thereof. For example, administration of a compound of the invention can take place prior to, after or at the same time as administration of the additional therapeutic agent(s). For example, a total treatment period can be decided for the compound of the invention. The additional agent(s) can be administered prior to the onset of treatment with the compound of the invention or following treatment with the compound of the invention. In addition, the additional agent(s) can be administered during the period of administering the compound of the invention but does not need to occur over the entire treatment period. In another embodiment, the treatment regimen includes pre-treatment with one agent, followed by the addition of the other agent or agents. Alternating sequences of administration are also contemplated. Alternating administration includes administration of a compound of the invention, followed by the additional agent, followed by a compound of the invention, etc. The therapeutic efficacy of the combination of a compound of the invention and the additional agent(s) is at least additive. In some embodiments, the therapeutic efficacy is synergistic, namely the overall dose of each of the components may be lower, thus resulting in significantly lower side effects experienced by the subject, while a sufficient antiviral effect is nonetheless achieved.

In another embodiment, the pharmaceutical composition that comprises a compound having anti-viral activity of any of formulae I, VII, VIII, IX or X as defined herein as active ingredient, may further comprise a pharmaceutically acceptable carrier or excipient.

A pharmaceutically acceptable carrier or excipient may be any material with which the active ingredient is formulated to facilitate administration. A carrier or excipient may be a solid or a liquid, including a material which is normally gaseous but which has been compressed to form a liquid, and any of the carriers or excipients normally used in formulating pharmaceutical compositions. Typically, compositions according to the invention contain 0.5 to 95% by weight of active ingredient.

The compounds of the present invention can be formulated as, for example, tablets, pills, capsules, pellets, granules, powders, lozenges, sachets, cachets, elixirs, suspensions, dispersions, emulsions, solutions, syrups, aerosols, ointments, soft and hard gelatin capsules, suppositories, sterile injectable solutions, and sterile packaged powders. Each possibility represents a separate embodiment of the present invention. These formulations can be produced by known methods using conventional solid carriers or excipients such as, for example, lactose, starch or talcum or liquid carriers such as, for example, water, fatty oils or liquid paraffins. Other carriers or excipients which may be used include, but are not limited to, materials derived from animal or vegetable proteins, such as the gelatins, dextrins and soy, wheat and psyllium seed proteins; gums such as acacia, guar, agar, and xanthan; polysaccharides; alginates; carboxymethylcelluloses; carrageenans; dextrans; pectins; synthetic polymers such as polyvinylpyrrolidone; polypeptide/protein or polysaccharide complexes such as gelatin-acacia complexes; sugars such as mannitol, dextrose, galactose and trehalose; cyclic sugars such as cyclodextrin; inorganic salts such as sodium phosphate, sodium chloride and aluminium silicates; and amino acids having from 2 to 12 carbon atoms and derivatives thereof such as, but not limited to, glycine, L-alanine, L-aspartic acid, L-glutamic acid, L-hydroxyproline, L-isoleucine, L-leucine and L-phenylalanine. Each possibility represents a separate embodiment of the present invention.

Auxiliary components such as tablet disintegrants, solubilisers, preservatives, antioxidants, surfactants, viscosity enhancers, coloring agents, flavoring agents, pH modifiers, sweeteners or taste-masking agents may also be incorporated into the composition. Suitable coloring agents include, but are not limited to, red, black and yellow iron oxides and FD & C dyes such as FD & C blue No. 2 and FD & C red No. 40 available from Ellis & Everard. Suitable flavoring agents include, but are not limited to, mint, raspberry, liquorice, orange, lemon, grapefruit, caramel, vanilla, cherry and grape flavors and any combinations thereof. Suitable pH modifiers include, but are not limited to, citric acid, tartaric acid, phosphoric acid, hydrochloric acid and maleic acid. Suitable sweeteners include, but are not limited to, aspartame, acesulfame K and thaumatin. Suitable taste-masking agents include, but are not limited to, sodium bicarbonate, ion-exchange resins; cyclodextrin inclusion compounds, adsorbates or microencapsulated actives. Each possibility represents a separate embodiment of the present invention.

In certain embodiments, a delivery vehicle is used. An exemplary delivery vehicle for the pharmaceutical compositions of the present invention is a liposome. A liposome is capable of remaining stable in a subject for a sufficient amount of time to deliver a compound of the present invention to the subject. A liposome within the scope of the present invention is preferably stable in the subject into whom it has been administered for at least about 30 minutes, more preferably for at least about 1 hour and even more preferably for at least about 24 hours.

Suitable routes of administration of the compounds and compositions of the present invention include, for example, oral, rectal, transdermal, topical, transmucosal, especially transnasal, intestinal or parenteral delivery, including intramuscular, subcutaneous and intramedullary injections as well as intrathecal, direct intraventricular, intravenous, inrtaperitoneal, intranasal, intraarterial, intravesicle (into the bladder) or intraocular injections. Each possibility represents a separate embodiment of the present invention.

According to certain aspects and embodiments, the compounds and compositions of the present invention are particularly suitable for oral administration. It is contemplated that by orally administering the compounds and compositions of the present invention, a systemic effect can be achieved. In one embodiment, the compounds and compositions of the present invention are administered through nasal respiratory route. Compositions in pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, orally or nasally, from devices that deliver the composition in an appropriate manner.

Solutions or suspensions used for parenteral, intradermal, or subcutaneous application typically include the following components: a sterile diluent such as water for injection, saline solution, fixed oils, polyethylene glycols, glycerine, propylene glycol (or other synthetic solvents), antibacterial agents (e.g., benzyl alcohol, methyl parabens), antioxidants (e.g., ascorbic acid, sodium bisulfite), chelating agents (e.g., ethylenediaminetetraacetic acid), buffers (e.g., acetates, citrates, phosphates), and agents that adjust tonicity (e.g., sodium chloride, dextrose). The pH can be adjusted with acids or bases, such as hydrochloric acid or sodium hydroxide, for example. The parenteral preparation can be enclosed in ampules, disposable syringes or multiple dose glass or plastic vials.

Pharmaceutical compositions adapted for parenteral administration include, but are not limited to, aqueous and non-aqueous sterile injectable solutions or suspensions, which can contain antioxidants, buffers, bacteriostats and solutes that render the compositions substantially isotonic with the blood of an intended recipient. Such compositions can also comprise water, alcohols, polyols, glycerine and vegetable oils, for example. Extemporaneous injection solutions and suspensions can be prepared from sterile powders, granules and tablets. Such compositions preferably comprise a therapeutically effective amount of a compound of the invention and/or other therapeutic agent(s), together with a suitable amount of carrier so as to provide the form for proper administration to the subject.

The administration regimen can be determined by a skilled artisan depending on the infection and the severity of the condition, the patient population, age, weight etc. The amount of a compound of the invention that will be effective in the treatment of a particular disorder or condition, including HCMV, will depend on the nature of the disorder or condition, and can be determined by standard clinical techniques. In addition, in vitro assays, animal assays (e.g. the guinea pig trans-placental transmission model and the newborn mouse model) and the ex-vivo assay described herein below, may optionally be employed to help identify optimal dosage ranges. The precise dose to be employed also depends on the route of administration, and the progression of the disease or disorder, and should be decided according to the judgment of the practitioner and each patient's circumstances. Typically dosage in the range of 0.01-1000 mg/kg of body weight, 0.1 mg/kg to 100 mg/kg, 1 mg/kg to 100 mg/kg, 10 mg/kg to 75 mg/kg, etc. may be used. Exemplary, non-limiting amounts of the compounds of the present invention include 0.1 mg/kg, 0.2 mg/kg, 0.5 mg/kg, 1 mg/kg, 5 mg/kg, 10 mg/kg, 20 mg/kg, 50 mg/kg, 60 mg/kg, 75 mg/kg and 100 mg/kg. Each possibility represents a separate embodiment of the present invention. Alternatively, the amount administered can be measured and expressed as molarity of the administered compound. By way of illustration and not limitation, a compound of the present invention (e.g. a compound of any of formulae I, VII, VIII, IX, or X) can be administered in a range of 0.1 μM to 10 mM, e.g., about 0.1 μM, 10 μM, 100 μM, 1 mM, and 10 mM. Alternatively, the amount administered can be measured and expressed as mg/ml, μg/ml, or ng/ml. By way of illustration and not limitation, an anti-viral agent can be administered in an amount of 1 ng/ml to 1000 mg/ml, for example 1-1000 ng/ml, 1-100 ng/ml, 1-1000 μg/ml, 1-100 μg/ml, 1-1000 mg/ml, 1-100 mg/ml etc. Effective doses may be extrapolated from dose-response curves derived from in vitro, animal model or ex-vivo model test bioassays or systems.

The administration schedule can be taken once-daily, twice-daily, thrice-daily, once-weekly, twice-weekly, thrice-weekly, once-monthly, twice-monthly, thrice-monthly, or any other administration schedule known to those of skill in the art. In addition, the administration can be continuous, i.e., every day, or intermittently. The terms "intermittent" or "intermittently" as used herein means stopping and starting at either regular or irregular intervals. For example, intermittent administration can be administration in one to six days per week or it may mean administration in cycles (e.g. daily administration for two to eight consecutive weeks, then a rest period with no administration for up to one week) or it may mean administration on alternate days.

The following examples are presented in order to more fully illustrate some embodiments of the invention. They should, in no way be construed, however, as limiting the broad scope of the invention.

EXPERIMENTAL DETAILS SECTION

Example 1: Highly Potent Anti-Viral Activity of Artemisone and Compound IX as Determined by Plaque Reduction Assay Materials and Experimental Methods
Virus, Cells, and Tested Compounds The CMV strains used were: AD169 (obtained from the American Type Culture Collection), and TB40/E. In addition, low-passage clinical isolates CI704, and CI893, recovered at the Hadassah Clinical Virology Laboratory from the urine of congenitally-infected newborns, and propagated for 3-5 passages, were used for some experiments. All CMV strains were propagated and titered in human foreskin fibroblasts (HFF) cells. Cell-free virus stocks and cell-associated clinical isolates were maintained at −70° C. Viral stocks were titered by serial 10-fold dilution in 24-well tissue culture plates containing HFF monolayers overlaid with agarose-medium. After incubation for 7 to 10 days, plaques were enumerated, and virus titer was determined as plaque forming units (PFU) per milliliter (ml). Stocks of artemisone, artemiside, RW177, compound IX, and artesunate were freshly prepared at 10 mM concentration in DMSO. Ganciclovir, stored as 10 mM stock was used in comparative assays.

Plaque Reduction Assay

Cell monolayers were inoculated in 24-well culture plates with 0.2 ml of virus suspension containing 60 to 100 PFU per well. After adsorption for 60 min at 37° C., the inoculum was removed, and culture medium was replaced with agarose-medium overlay containing the tested drug. The following final drug concentrations were used: Artemisone: 0, 0.1, 1, 5, 10, 25, and 50 μM; Artesunate: 0, 1, 5, 10, 25, 50, and 100 μM; Ganciclovir, artemiside, compound IX and RW177: 0, 0.1, 1, 5, 10, 25, and 50 μM. Plates were incubated for 10 days at 37° C. in a 5% $CO_2$ incubator. Plaques were then counted microscopically. The drug concentration required to reduce the number of plaques to 50% of the control value ($IC_{50}$), was calculated.

Results

Figure 2A:
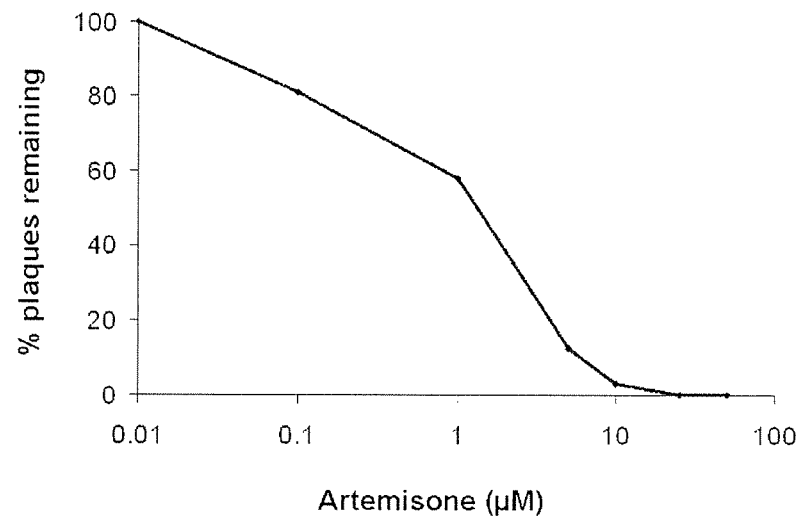
FIGS. 2A-2B.
Figure 3A:
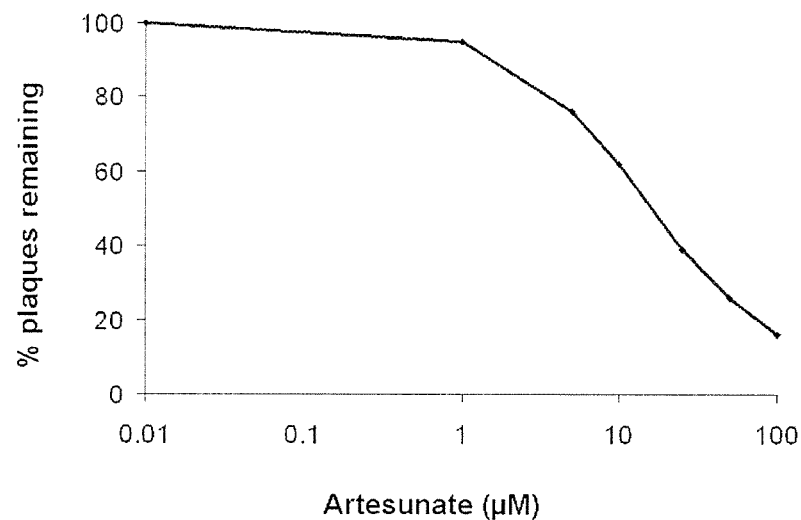
FIGS. 3A-3B.

Antiviral activity of artemisone was determined by applying various drug concentrations to a growing virus in cell culture, using a standard plaque reduction assay. Artesunate, a compound known to have significant anti-viral activity, was tested in parallel. Ganciclovir was used as an additional positive control. The $IC_{50}$ values of at least three separate experiments with each drug and virus were averaged, and the results are reported as mean±standard deviation values. Representative curves of plaque reduction assay for artemisone and artesunate are depicted in FIGS. 2A and 3A, respectively. Artemisone exhibited similar antiviral activity (0.9±0.3 μM) to that of ganciclovir, while demonstrating no cytotoxicity. By comparison, the mean $IC_{50}$ value of artesunate was 10.8±4.2 μM. Thus, artemisone possesses enhanced antiviral efficacy far superior to that of artesunate Importantly, artemisone demonstrated broad CMV antiviral activity against both laboratory-derived CMV strains and low-passage CMV clinical isolates. Superior antiviral activity of artemisone compared to artesunate was also demonstrated in an additional cell-type culture system of retinal epithelial cells (RPE). The CMV antiviral activity of compound IX was also found to be superior with $IC_{50}$ values of 2.1±0.6 µM. Hence, compound IX of the present invention can also be used as an effective anti-CMV agent.

In contrast, the 10-alkylamino artemisinin derivatives artemiside and RW177 (FIG. 1), which possess enhanced activity against parasites, had significantly inferior antiviral activity ($IC_{50}$ values >40 µM), emphasizing the enhanced and surprising antiviral activity of artemisone and compound IX.

Example 2: Confirmation of Highly Potent Anti-Viral Activity of Artemisone by Viral DNA Quantitation Materials and Experimental Methods
Quantification of Viral DNA Viral DNA quantity in infected cells with and without added drugs (expressed as genome copies/well) was determined by real-time PCR assay, following DNA extraction from cells, with the use of primers and probe derived from the CMV gB gene. The assay is known to demonstrate a linear quantitation over a 6-log range with a sensitivity of 50 copies/ml.

Results

Figure 2B:
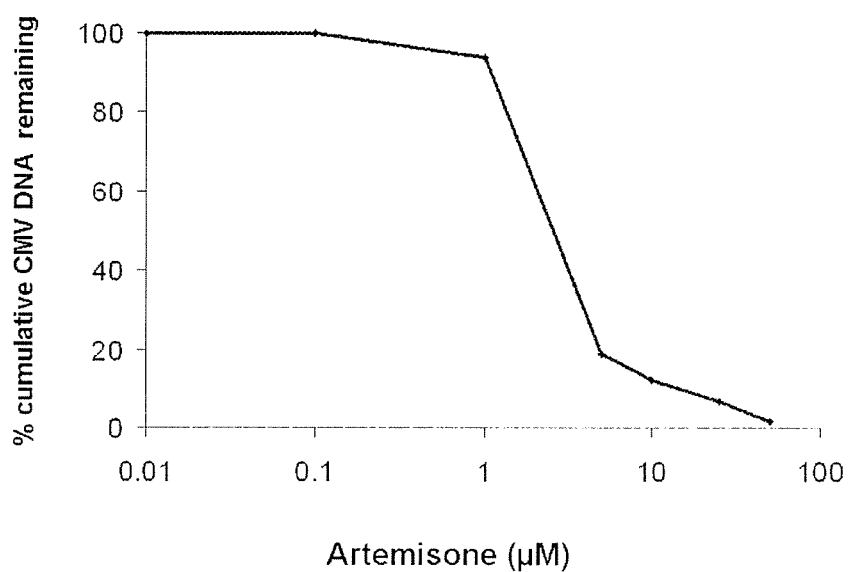
Figure 3B:
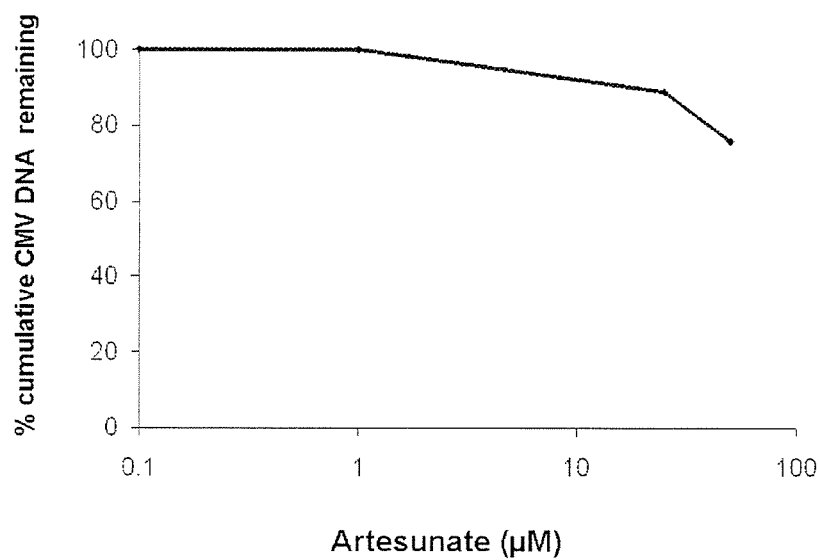

The results of Example 1 were confirmed by quantitation of viral DNA using real-time PCR. These assays confirmed that artemisone possesses enhanced antiviral efficacy, far superior to that of artesunate. Representative curves of viral DNA accumulation for artemisone and artesunate are depicted in FIGS. 2B and 3B, respectively.

Thus, antiviral susceptibility and viral DNA quantitation assays revealed that artemisone is a highly effective inhibitor of CMV replication and viral DNA synthesis.

Example 3: Artemisone Effectively Inhibits CMV Immediate Early (IE) Gene Expression Materials and Experimental Methods
Analysis of Viral Gene Expression Human foreskin fibroblasts (HFF) were infected with HCMV strain AD169. At 1 hour post infection (hpi), artemisone (25 µM) or ganciclovir (25 µM) were added to the growth medium, and the cells were further incubated in the presence of the drug, until prepared for immunofluorescence analysis at 24 and 72 hpi—to analyze the expression of IE and pp65, respectively. Control untreated infected cells, and mock-infected cells were analyzed in parallel.

Immunofluorescence Assay

Cells grown on 8-well glass slides were infected at a multiplicity of infection (moi) of 0.1 PFU/cell. Supernatant was removed at 24 and 72 hpi, and cells were washed 3 times with PBS and fixed with 3.7% formaldehyde for 30 minutes at room temperature. Cells were washed 5 times with PBS+1% $NH_4Cl$, permeabilized by 0.1% TX100 for 5 minutes and washed 5 times with PBS+1% $NH_4Cl$. After 1 hour of blocking using 1% BSA in PBS, the indicated primary monoclonal antibodies (IE1/2 or pp65) were added to the cells in appropriate dilution in 0.5% BSA in PBS and incubated either at room temperature for 2 hours or overnight at 4° C. The secondary antibody was added to the cells in appropriate dilution in PBS containing 0.5% BSA for 30 minutes at room temperature and washed by PBS.

Following mounting with commercial mounting media, with addition of 4',6-diamidino-2-phenylindole (DAPI) nuclear stain (yielding nuclear blue stain in all cells), the cells were analyzed by fluorescence microscopy. Results were monitored on at least 3 independent experiments, scoring at least 5 fields (of between 500 and 800 cells each) for each treatment arm.

Results

Figure 4:
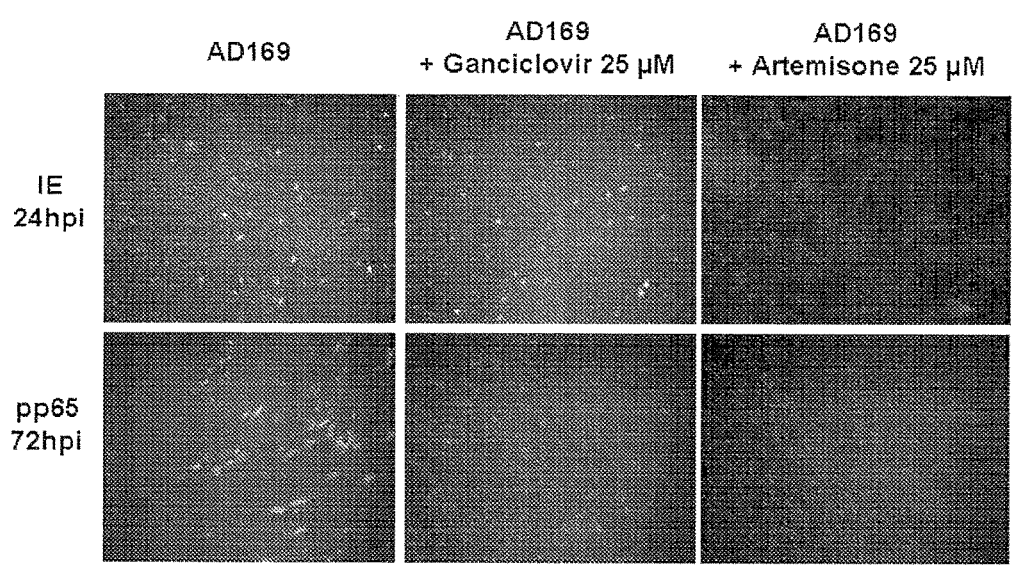
FIG. 4: Immunofluorescence microscopy of the expression of CMV immediate early (IE) and early-late (pp65) viral genes 24 and 72 hours post infection (hpi).
Figure 5A:
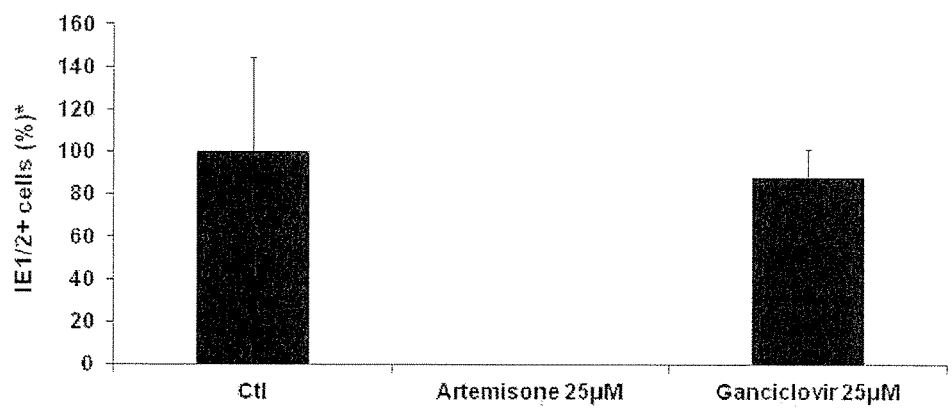
FIGS. 5A-5B.

Representative immune-fluorescence images obtained in artemisone and ganciclovir-treated infected cells are depicted in FIG. 4. Artemisone treatment resulted in a significant reduction of viral IE gene expression at 24 hpi. This is in sharp contrast to the results obtained when treating with ganciclovir, which did not inhibit IE gene expression (Table 1; FIG. 5A).

Figure 5B:
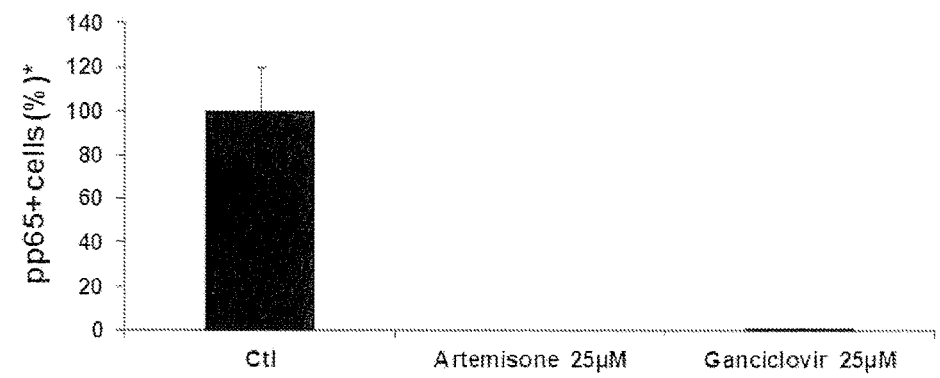

Consistent with the reduction in IE gene expression, artemisone treatment, as ganciclovir, resulted in a highly efficient reduction of viral late (pp65) gene expression (Table 1; FIGS. 4, 5B).

TABLE 1

Cell count results of total and HCMV antigen-positive cells.

| Drug treatment/ analyzed CMV antigen | Total cells counted per field (N)* | CMV antigen-positive cells per field (N)* | CMV antigen-positive cells (%) |
|---|---|---|---|
| Control untreated/ IE1 ± IE2 | 664 ± 23 | 45 ± 20 | 6.78 |
| Artemisone/ IE1 ± IE2 | 765 ± 31 | 0 | 0 |
| Ganciclovir/ IE1 ± IE2 | 553 ± 42 | 33 ± 5 | 5.97 |
| Control untreated/ pp65 | 647 ± 67 | 115 ± 23 | 17.77 |
| Artemisone/ pp65 | 798 ± 43 | 0 | 0 |
| Ganciclovir/ pp65 | 555 ± 22 | 1 ± 0.25 | 0.18 |

*At least 5 fields were counted in each experiment.

Whereas ganciclovir does not inhibit HCMV immediate early (IE) gene expression, artemisone effectively inhibits IE gene expression and both artemisone and ganciclovir effectively inhibit HCMV late gene expression. Thus, without being bound by any theory or mechanism of action it is contemplated that artemisone demonstrates a novel mechanism of action, different from that of ganciclovir, which involves inhibition of a very early step of viral replication preceding viral DNA synthesis.

Example 4: Combination Therapy with Artemisone

To investigate the effect of the artemisone treatment on the efficacy of conventional anti-HCMV drugs, HCMV-infected cells were treated with a combination of artemisone and ganciclovir. Using intermediate concentrations of ganciclovir (1 µM), the combined treatment with artemisone led to additive inhibitory effects on HCMV replication.

Example 5: Evaluating Therapeutic Efficiency

In order to evaluate the therapeutic efficacy of the anti-CMV compounds of the present invention, an ex-vivo model of HCMV infection in maternal decidua is used as described in J. Virol., 2011; 85: 13204-13213, the content of which is hereby incorporated in its entirety. In particular, the study of HCMV transmission and pathogenesis is largely limited by the absence of animal models for HCMV infection. While the guinea pig trans-placental transmission model and the newborn mouse model have proven invaluable for the experimental evaluation of vaccines and virus-induced brain-pathology, the species specificity of HCMV has precluded experimental modeling of congenital human infection. The ex-vivo infected decidual cultures can serve as a unique surrogate human model for screening therapeutic treatments. Using the ex-vivo model, the various physiological and pathological processes occurring in response to treatment with the artemisinin derivatives of the present invention, can be monitored thereby enabling the determination of the efficacy of treatment.

Materials and Experimental Methods
Cells and Viruses

Primary human foreskin fibroblasts (HFF) were used to propagate and isolate HCMV strains as described in Wolf et al., PNAS, 2001, 98, 1895-900; and Wolf et al., J. Clin. Invest., 1995, 95, 257-63, the content of each of which is hereby incorporated in its entirety. HFF were grown in Dulbecco's Modified Eagle's Medium (DMEM) supplemented with 10% fetal bovine serum, 2 mM glutamine, 100 IU/ml penicillin, 100 µg/ml streptomycin (Biological industries, Beit Haemek, Israel) and 0.25 µg/ml fungizone (Invitrogen, CA, USA). The HCMV strains used were AD169 (obtained from the American Type Culture Collection), TB40/E strain expressing UL32-fused GFP (provided by C. Sinzger, Germany), TB40/E strain expressing UL83-fused GFP (strain RV1305; provided by M. Winkler, Germany), and CMVPT30-gfp, a cell-free HCMV clinically-derived strain expressing GFP (PT30). These viral strains were maintained as cell-free viral stocks. In addition, the low-passage clinical isolate CI851, recovered at the Hadassah Clinical Virology Laboratory from the urine of a congenitally-infected newborn, and propagated for 3-5 passages as cell-associated virus was used. A cell-free stock of CI851 was prepared by sonication of infected cells, followed by removal of pelleted cellular debris. Virus titers of the cleared supernatants were determined by the standard plaque assay on HFF.

Preparation and Infection of Decidual Organ Cultures

Decidual tissues from women undergoing first-trimester elective pregnancy terminations were obtained by deep scraping to obtain maternal tissue from the basal plate and placental bed encompassing the decidua with interstitial trophoblastic invasion. The study was approved by the Hadassah Medical Center Institutional Review Board, and performed according to the Declaration of Helsinki, Good Clinical Practice guidelines, and the Human-Experimentation Guidelines of the Israeli Ministry of Health. All donors gave written informed consent. Tissues, delivered within 4 hours after surgery, were kept on ice until sectioning. For preparation of decidual organ cultures, tissues were washed with phosphate buffered saline (PBS), cut by a microtome (Tissue Sectioner, TC-2, Sorvall Corp.) into thin slices (250 µm thickness) encompassing ~10 cell layers, and incubated in DMEM with 25% Ham's F12, 10% fetal bovine serum, 5 mM HEPES, 2 mM glutamine, 100 IU/ml penicillin, 100 µg/ml streptomycin (Biological industries, Beit Haemek, Israel), and 0.25 µg/ml fungizone in 37° C., 5% $CO_2$.

For infection of decidual organ cultures, the tissues were placed in 48-well plates (~5 slices/well to maintain optimal viability) immediately after the sectioning and inoculated with the indicated virus ($10^4$ plaque forming units/well, unless indicated otherwise) for 12 hours to allow effective viral adsorption. Following viral adsorption, the cultures were washed extensively and further incubated for the duration of the experiment with replacement of the culture medium every 2-3 days.

Tissue Viability Monitoring

Mitochondrial dehydrogenase enzyme (MTT) assay: Tissue slices were incubated with the MTT substrate (3-[4,5-dimethylthiazol-2-yl-2,5-diphenyltetrazolium bromide]) (Sigma, Israel) for 1 hour at 37° C. and then washed in PBS, followed by addition of 100% ethanol to dissolve the product colored crystals. The absorbance of four replicate samples was read using an ELISA plate reader (Organon Teknika, the Netherlands) at a wavelength of 540 nm in reference to 650 nm. The viability was determined by normalization of the absorbance values for the protein content of each extract as tested by the Bradford assay (Kolodkin-Gal et al., 2008, J. Virol., 82, 999-1010).

Glucose consumption assay: Glucose levels in the medium of the incubated tissues were monitored after 48 hours of culture by the Accu-check™ blood-sugar sensing device (Roche, Germany).

Histological and Immunohistochemistry Analysis

Decidual tissues were fixed in 37% formalin, embedded in paraffin, and cut into 5 µm sections. The sections were deparaffinized in xylene, rehydrated, and stained with hematoxylin and eosin (H&E).

For immunohistochemical detection of HCMV antigens, tissue sections were placed in 0.01M citrate buffer and warmed in a water bath to 90° C. for 15 minutes, allowed to cool to room temperature, followed by incubation with primary mouse monoclonal antibodies (mAbs) against HCMV diluted in CAS-block (Zymed Laboratories, CA, USA); immediate early (IE), pp65, or gB antigens (1:1000 dilution; Virusys Corporation, Taneytown, Md., USA) or CAS-Block containing no $1^{st}$ antibody to serve as a negative control. Sections were then washed and incubated with HRP-conjugated goat anti-mouse secondary antibody (Biocare Medical, CA, USA). The sections were washed again, and HCMV antigens were detected by the HRP substrate 3,3'Diaminobenzidine (DAB), followed by counterstaining with hematoxylin.

Immunofluorescence

Tissue specimens for immunofluorescence staining were fixed in 4% paraformaldehyde, embedded in OCT, flash frozen in liquid nitrogen and cut into 10 µm sections. Frozen sections were treated with CAS-Block in order to avoid nonspecific antibody binding, and incubated with CAS-Block only or CAS-Block containing the following antibodies for specific cell markers: mAbs against cytokeratin 7 (1:300 dilution, Dako Glostrup, Denmark) were used for the detection of CTBs; mAbs against vimentin (1:100 dilution, Dako) were used for the detection of decidual stromal cells; mAbs against CD11c (1:50 dilution, Biolegend, CA, USA) were used for the detection of dendritic cells; mAbs against CD68 (1:200 dilution, Abcam, Cambridge, UK) were used for the detection of macrophages, and rabbit polyclonal antibodies against von Willebrand factor (1:800 dilution, Dako) were used for the detection of endothelial cells. Sections were washed and incubated with cy5-conjugated goat anti-mouse or cy5-conjugated goat anti-rabbit secondary antibodies (1:200 dilution, Jackson Immunoresearch, PA, USA), and mounted in Vectashield mounting media with 4',6-diamidino-2-phenylindole (DAPI) nuclear stain (Vector Laboratories, Burlingame, Calif.). Slides were visualized using a Zeiss LSM710 Axio Observer.z1.confocal microscope, and analyzed using Zen 2009 software.

HCMV DNA and RNA Quantification

Infected decidual tissues and HFF cell cultures were washed extensively and stored at −70° C. along with their corresponding supernatants (harvested 2 days after last medium replacement).

DNA and RNA were extracted from the samples using the QIAamp DNA Mini Kit extraction kit and RNeasy Mini Kit (QIAGEN, Hilden, Germany) respectively, according to the manufacturer's instructions. The purified DNA samples were subjected to a quantitative real-time PCR reaction on a 7900HT Real Time PCR system (Applied Biosystems, Foster City, Calif., USA), using primers and probes derived from the HCMV glycoprotein B (gB) as described in Boeckh et al., 2004, J. Clin. Microbiol., 42, 1142-1148. The assay demonstrated a linear quantitation over a 6-log range. The purified RNA samples were subjected to reverse transcription using GoScript™ (Promega, Madison, USA), followed by quantitative real-time PCR of the late HCMV R160461 spliced mRNA as described in White et al., 2004, J. Virol., 78, 1817-1830. For comparative and kinetic analyses, the viral DNA copy number in tissues and HFF cell cultures was normalized by the cellular single-copy gene RNase P. RNase P was quantified using the Taqman RNase P kit (Applied Biosystems) according to the manufacturer's instructions. The viral mRNA copy number was normalized by the cellular house keeping gene G6PD.

Antiviral Treatments and Assays

The antiviral drugs ganciclovir and acyclovir (Sigma) were used at concentrations of 25 µM, 50 µM, 250 µM and 500 µM. The drugs were added to the culture medium after virus adsorption.

To measure neutralization by antibodies, the indicated virus strain was pre-incubated with HCMV HIG (Megalotect; 100 mg protein/50 IU per ml; Biotest, Germany) at 1:10, 1:100, and 1:1000 dilutions for 1 hour at room temperature, followed by inoculation of the pre-incubated virus-antibody mix on the tissues.

In post-adsorption treatment experiments, the same dilutions of HCMV HIG were added to the culture medium at 24 hours after viral adsorption, following extensive washing to remove loosely bound virus.

The tissues were further incubated in the presence of the drug or antibodies for the duration of the experiment. Drugs or antibodies were re-supplemented upon medium replacements.

Antiviral drug susceptibility was assayed by determining the drug concentration required to reduce the normalized tissue viral DNA copy number by 50% ($IC_{50}$), employing at least 5 independent replicate experiments per drug.

Results

Establishment of a Decidual Organ Culture

Figure 6A:
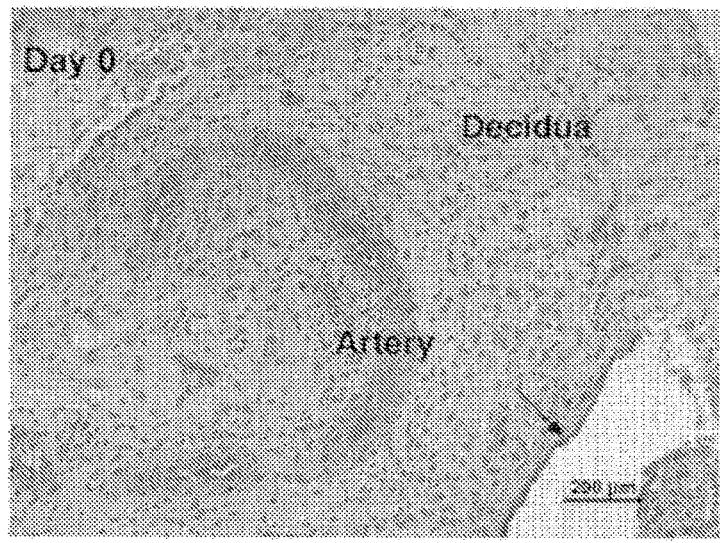
FIGS. 6A-6F: Histopathological analysis of HCMV infected and uninfected decidual organ cultures.
Figure 6B:
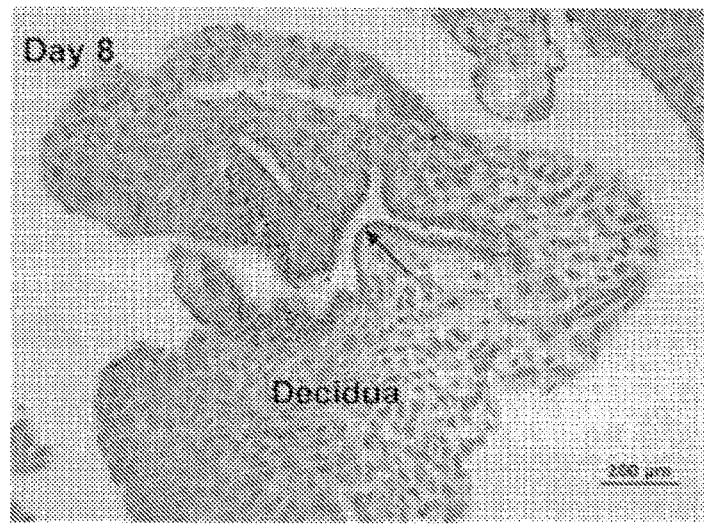

Fresh first-trimester decidual tissues were sectioned into thin slices (250 µm thickness), to ensure nutrients accessibility. Decidual organ cultures were placed in 48-well plates (~5 slices/well) immediately after sectioning, incubated in enriched DMEM and subjected to frequent media changes to maintain optimal viability. Decidual tissue viability, as monitored by both the MTT and glucose consumption assays, was maintained for at least 12 days of incubation ex-vivo. Furthermore, histological examination of sections obtained upon institution (day 0) and at 8 days of culture demonstrated preservation of typical decidual morphological features with no visible signs of cell death (FIGS. 6A-6B). Thus, the decidual explants remain viable and retain natural morphology over the time needed to support and monitor HCMV infection and spread which typically occurs within 4-7 days.

HCMV Infection Kinetics in the Decidua

To evaluate the susceptibility of decidual organ cultures to HCMV, decidual cultures were infected with the cell-free clinically-derived strain PT30, expressing GFP (Fox-Canale et al., 2007, Virology, 369, 55-68). This strain, which was shown to maintain a broad cell tropism to HFF, umbilical vein endothelial cells, and retinal epithelial cells, was chosen to represent the wide in vivo cell tropism of HCMV and provide visual monitoring of the infection.

Figure 6C:
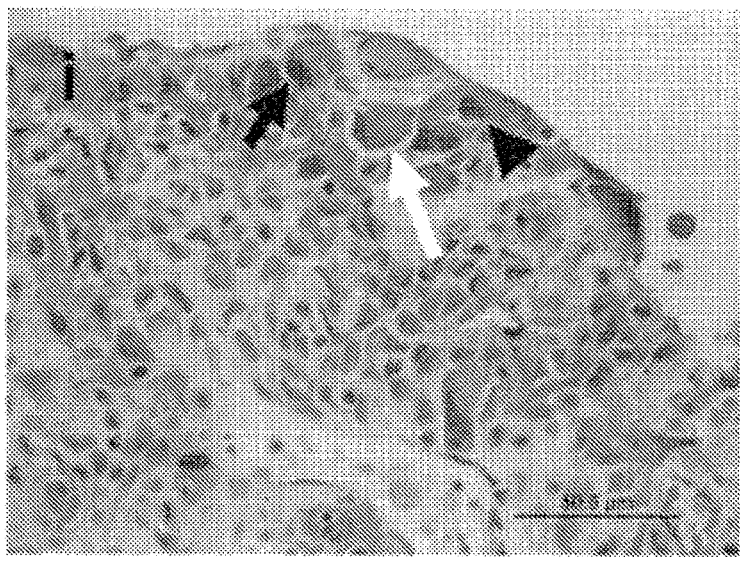
Figure 6D:
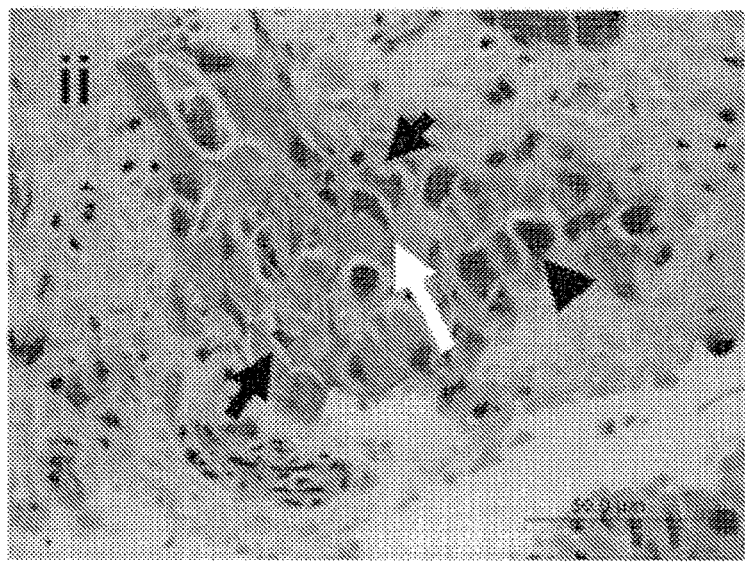

To evaluate the histopathological features of ex-vivo infected decidua, histological sections of infected tissues were examined at 6 dpi. Histology sections of the ex-vivo infected tissues exhibited the typical histopathological characteristics of natural HCMV infection, with the appearance of cytomegalic cells with "owl's eye" inclusion bodies, granular cytoplasmic inclusions, and irregular hyperchromatic nuclei (FIGS. 6C-6D).

Figure 6E:
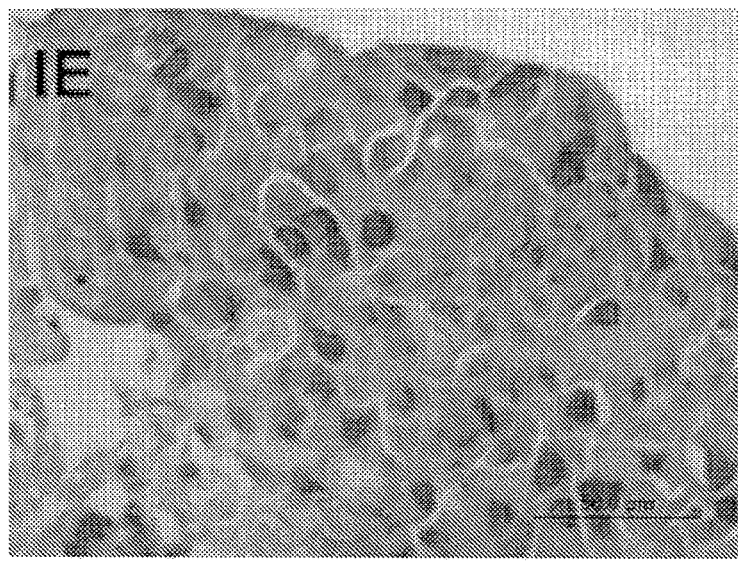
Figure 6F:
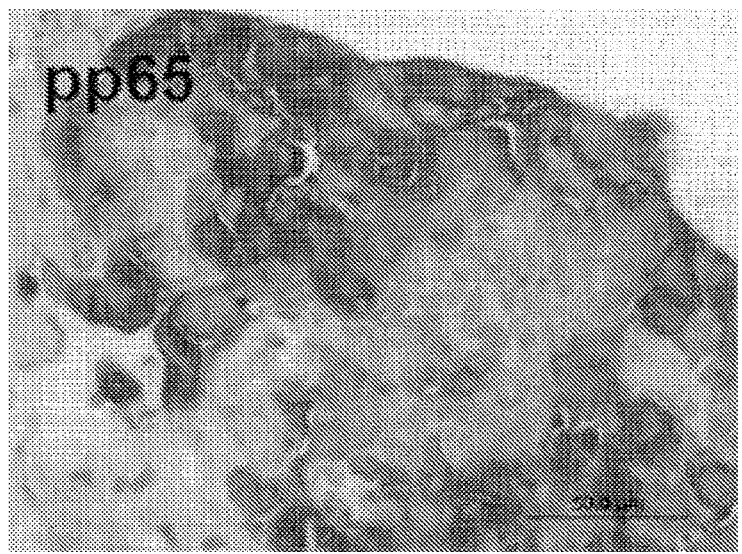

Immunohistochemical analysis of the infected sections revealed the expression of both immediate early, and pp65 early-late viral genes (FIGS. 6E-6F), as well as gB (known to be expressed late after infection). All control tissues, including mock-infected sections and infected sections reacted with secondary antibodies only, were negative by immunohistochemical staining. These findings indicate that HCMV undergoes a full replication cycle in the infected decidua tissues.

To follow virus spread kinetics in the decidua, PT30 infected live tissues were monitored daily for GFP-expressing cells by confocal microscopy. As shown in FIGS. 7A-7D, GFP-expression was first detected at 2 days post infection (dpi), appearing in individual cells. Gradual progression of infection was noted by 3-7 dpi, along with the formation of plaque-like clusters of infected cells (FIGS. 7A-7D). This kinetics pattern of organ culture infection was consistently observed in more than 80 decidual tissues obtained from different subjects, and could be similarly monitored following infection with the endotheloitropic strain TB40/E, expressing GFP-fused to the late structural protein pp150.

Figure 8:
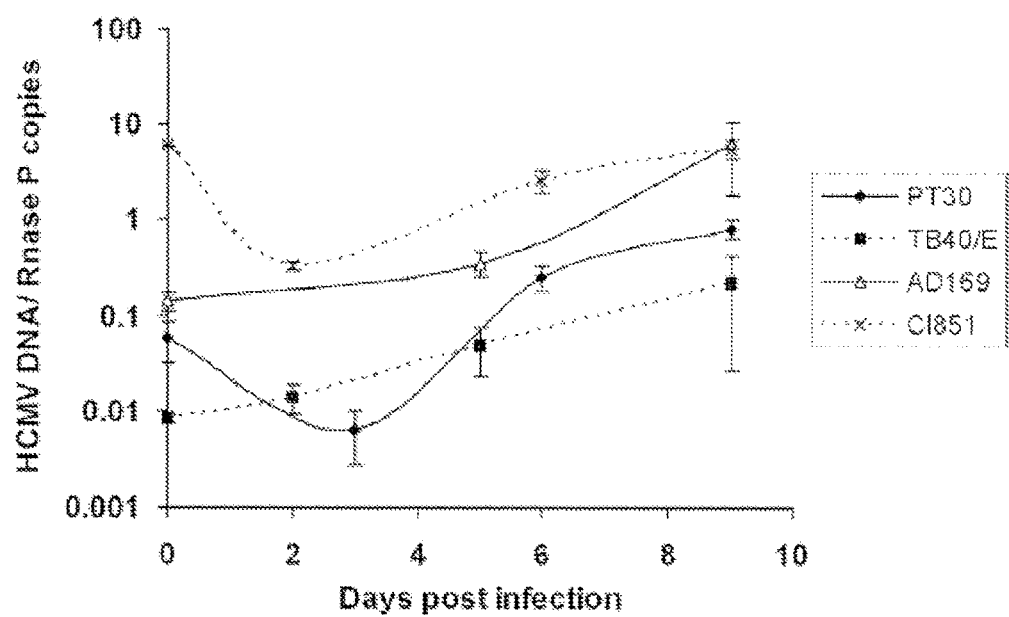
FIG. 8: HCMV infection kinetics in decidual cultures. Viral DNA accumulation in tissue lysates following infection with the indicated viral strains, normalized by RNase P gene DNA copies. PT30: ♦; TB40/E: ■; AD169: Δ; and CI851: x.

To further quantify progression of infection over time, the accumulation of viral DNA in the infected decidual cultures by real-time PCR following infection ($10^4$ PFU/well) with strains PT30, TB40/E, AD169, and the low-passage clinical strain CI851 was measured. As shown in FIG. 8, there was a consistent increase in tissue-associated viral DNA with time (above the level of the remaining input DNA as detected at early times post infection) which was demonstrated for all viral strains: A 1.3 to 2-log increase in viral DNA accumulation was observed for all strains between 2-9 dpi, reflecting active DNA synthesis within the infected tissues. Moreover, a quantitative analysis of the HCMV true-late RNA R160461 demonstrated a 1.9 log rise within 7 dpi for both TB40/E and AD169. These findings, together with the spreading pattern of GFP expression (independently demonstrated for the 2 different GFP-expressing viral strains), and the expression of late viral proteins, support active viral replication in the decidual organ cultures.

HCMV Infects a Wide Range of Cells in the Decidua

Figure 9:
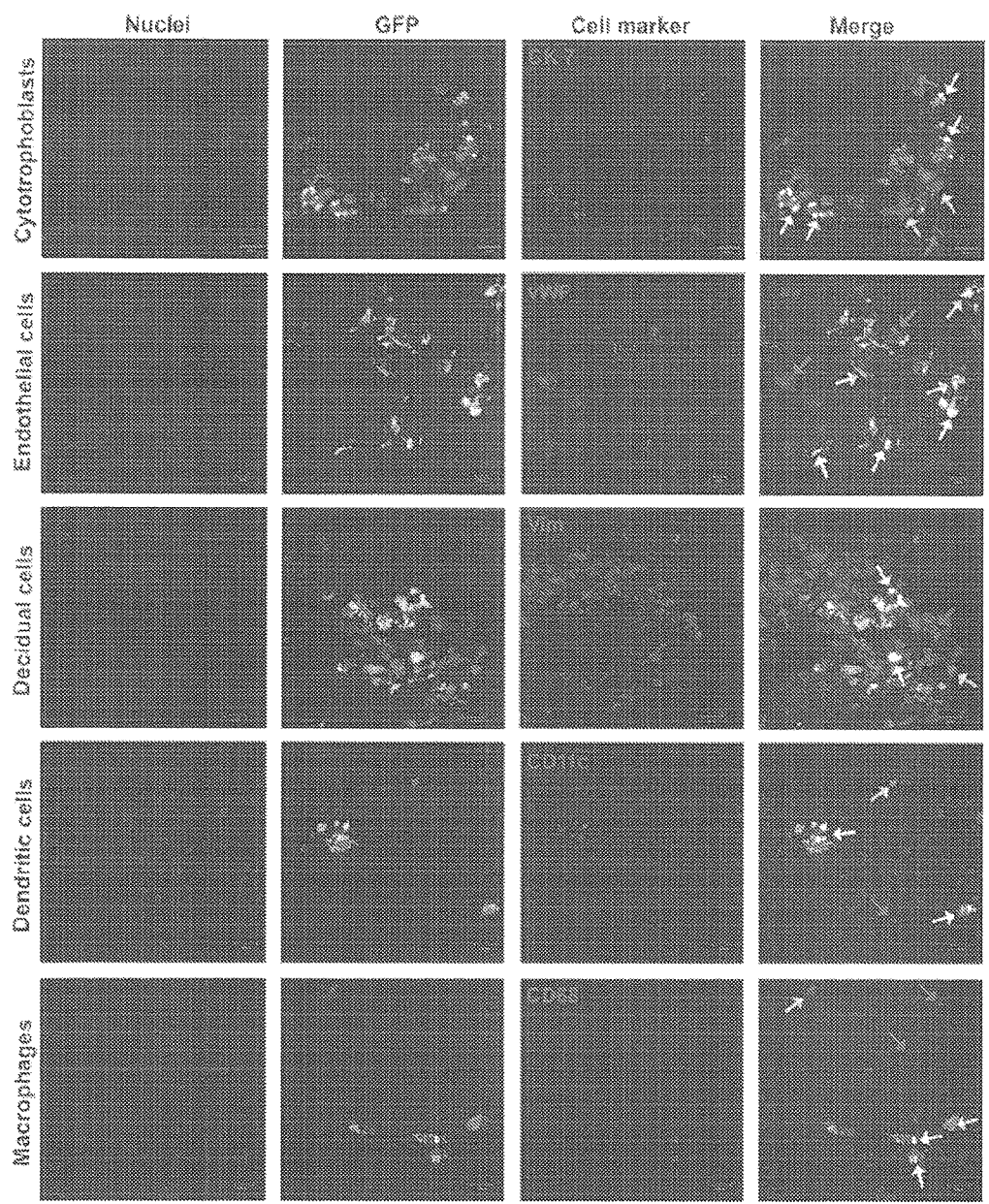
FIG. 9: Cellular tropism of HCMV in infected decidual cultures. At 10 dpi, frozen sections were prepared from decidual cultures infected with HCMV strain TB40/E expressing UL83 (pp65)-fused GFP, stained with monoclonal antibodies against the indicated cell types, and counterstained with DAPI to visualize the cell nuclei. Colocalization of the virus (marked by GFP) with specific cell markers was analyzed by confocal microscopy. Arrows point to cells exhibiting colocalization, infected cells with no colocalization with the specific cellular marker; and stained uninfected cells. CK7, cytokeratin 7; vWF, von Willebrand factor; Vim, vimentin.

While HCMV is characterized by a broad cell tropism in vivo, in vitro studies are generally limited to single cell-type cultures. To define the cellular tropism of HCMV within the decidua, the types of infected cells were identified. Decidual tissues infected by the clinically-derived strains TB40/E and PT30 (characterized by broad cell tropism) and the poorly-endotheliotropic strains AD169 were examined. Frozen sections of HCMV-infected tissues were analyzed by confocal immunofluorescence, using specific cell markers. FIG. 9 shows viral colocalization of strain TB40/E with markers of invasive cytotrophoblasts (Cytokeratin 7), endothelial cells (von Willebrand Factor), decidual cells (Vimentin), dendritic cells (CD11c), and macrophages (CD68). Similar cell tropism was shown for PT30, indicating ex-vivo infection of all major decidual cell types by HCMV. In parallel experiments following infection with strain AD169, viral colocalization only with vimentin-positive stromal-decidual cells can be demonstrated.

Inhibition of HCMV Infection of Decidual Organ Cultures

Recent studies have suggested the potential applicability of prenatal antiviral interventions in preventing maternal fetal transmission and congenital disease (Jacquemard et al., 2007 BJOG, 114, 1113-1121; and Nigro et al., 2005, N. Engl. J. Med., 353, 1350-1362). While all currently available anti-HCMV drugs (i.e. ganciclovir, foscarnet, and cidofovir) are considered teratogenic, new and alternative antiviral options, including acyclovir and HCMV HIG, have been explored.

To assess the efficacy of the decidual organ culture for evaluating antiviral activity, and to examine the ex-vivo effect of antiviral drugs on HCMV replication in the decidua, infected decidual cultures were incubated with different concentrations of ganciclovir and acyclovir. Decidual cultures were infected with HCMV strain TB40/E ($10^5$ PFU/well) and were incubated with increasing concentrations of ganciclovir (GCV) or acyclovir (ACV). Viral DNA in the treated and untreated decidual tissue lysates was quantitated at 8 dpi and values were normalized by RNase P DNA copies.

Figure 10:
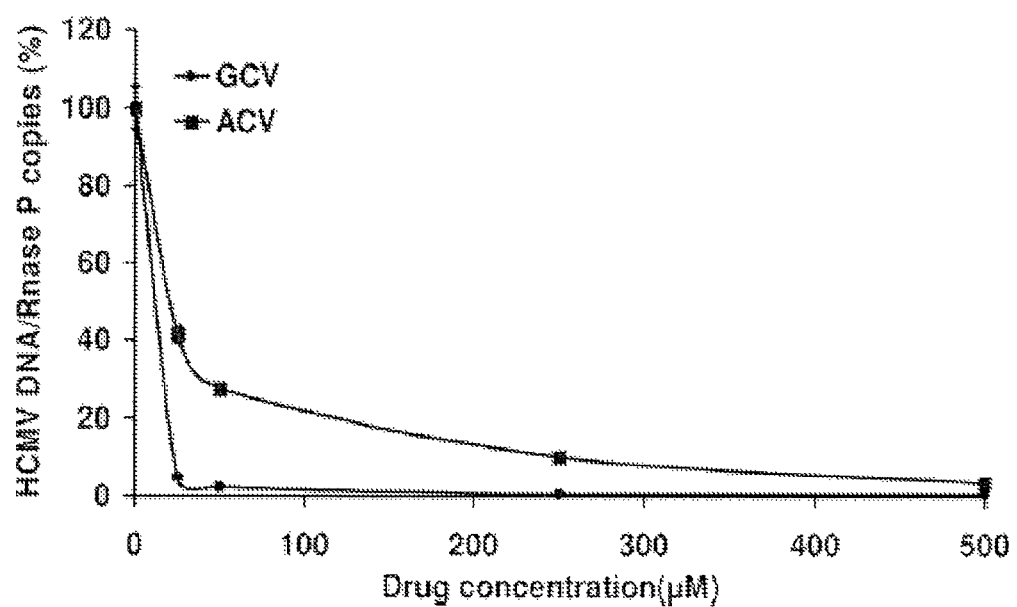
FIG. 10: Inhibition of HCMV infection in decidual organ cultures by antiviral drugs (GCV: ●; ACV: ■). The results are expressed as a percentage of the amount of normalized HCMV DNA present in untreated cultures±standard error. The error bars are not readily visible due to the low values for standard error. Significant differences were found between treated and untreated decidual cultures ($P<0.05$ by the two-tailed paired t test).

FIG. 10 shows that both antiviral drugs inhibited HCMV replication in the decidual cultures, as measured by dose-dependent reduction of viral DNA accumulation in the infected tissues. Ganciclovir exhibited a higher antiviral efficacy when compared to acyclovir ($IC_{50}$ of 1.5 μM versus 18.3 μM). These findings demonstrate that ex-vivo infected decidual cultures can serve to study the effect of antiviral interventions and to assess the therapeutic efficacy of the compounds of the present invention.

Figure 11A:
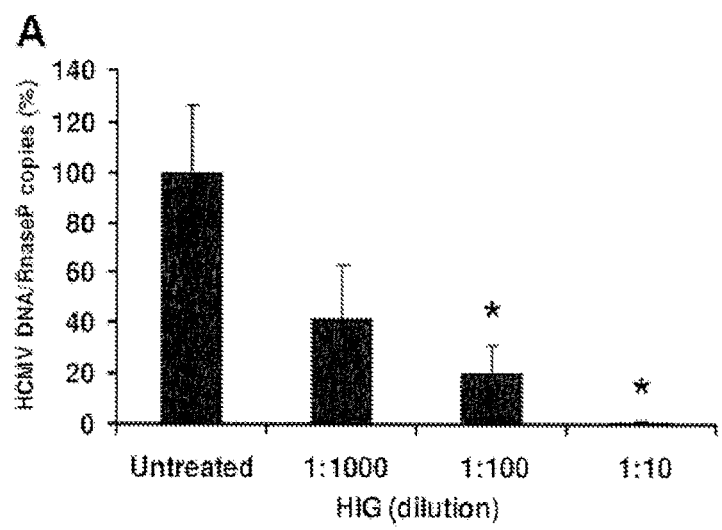
FIGS. 11A-11B: Neutralization and post adsorption inhibition of HCMV infection in decidual organ cultures by HCMV hyper immune globulins (HIG).
Figure 11B:
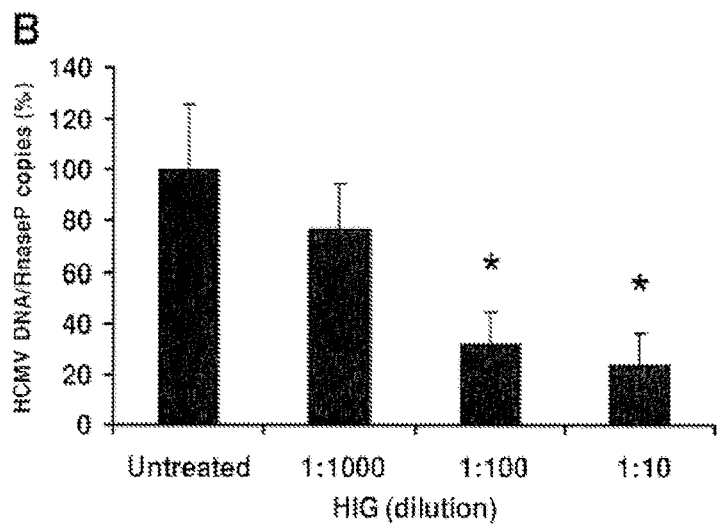

The antiviral effect of HCMV HIG in the infected decidual cultures was examined Studies of the neutralization activity showed that HCMV HIG preparation, when pre-incubated with the virus was capable of neutralizing HCMV infection of the decidua (FIG. 11A). The calculated HIG concentration for 50% viral neutralization was 36 μg/ml. No antiviral effect was observed with HCMV IgG-negative serum. This finding could correlate with the prophylactic effect of HIG in prevention of maternal-fetal transmission in vivo. It should be noted that the neutralizing activity of HCMV HIG in the decidual cultures was higher than the neutralizing activity in fibroblasts culture. In comparative experiments, the neutralization titer of HCMV HIG was more than 10-fold lower in the decidual cultures than in HFF cell cultures. To further examine the potential therapeutic effect of HIG, its antiviral activity when added after viral adsorption was examined. At 24 hours post-adsorption, tissues were extensively washed before the addition of increasing HIG dilutions to the culture media. A significant dose-dependent inhibition of HCMV replication was clearly demonstrated (FIG. 11B) with an $IC_{50}$ of 652 μg/ml. The inhibitory effect of HIG when added post-adsorption, was also evident by the reduction of spread of plaque-like clusters at late times post-infection. In contrast, no post-adsorption inhibitory effect was observed in HFF cell cultures. These studies reveal a combined neutralization and a post-adsorption antiviral effect of HCMV HIG in the decidua.

Thus, active viral replication in the tissue was demonstrated by 1) gradual progression of GFP-expressing cell foci following infection with GFP-expressing HCMV strains, along with a consistent increase in viral DNA over an interval of 2-9 days post infection; 2) expression of both immediate-early and true-late viral RNA and proteins in the infected organ cultures; 3) appearance of typical histopathological features of natural infection; and 4) a dose-dependent inhibition of viral spread and DNA accumulation by the antiviral DNA polymerase inhibitor ganciclovir. These combined findings demonstrate the ability of the ex-vivo infected decidual organ culture to address dynamic aspects of viral tropism and spread.

A wide range of cells which are infected by HCMV clinically-derived strains in the decidua was identified, including invasive CTBs, endothelial cells, macrophages, stromal decidual, and dendritic cells. This finding reflects the unique multi-cell-type nature of the decidua. The infected cells in the decidua represent the two distinct pathways of viral entry, i.e. fusion (at the cell surface) and endocytosis-mediated, as characterized in fibroblasts and in epithelial/endothelial cells, respectively. Whereas HCMV endocytosis-mediated entry has been shown to require the viral gH/gL/UL128-131 complexes, the UL128-131 proteins are not essential for HCMV fusion-mediated entry.

The combined virus neutralization and post-infection effect of HCMV HIG, demonstrates the capability of the ex-vivo model in the decidual organ cultures to evaluate the effect of new antiviral interventions in the maternal-fetal interface. For example, the infected decidual organ cultures could provide the mechanistic basis for clinical trials accessing prenatal prophylactic and therapeutic use of anti-HCMV drugs. The ex-vivo modeling of HCMV infection in a novel decidual organ culture revealed a broad target-cell range with consistent cell-to-cell mode of spread of both clinically- and laboratory-derived viral strains. This model can be used to evaluate the efficacy of the compounds of the present invention as new, effective and non-teratogenic anti-HCMV drugs.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

It should be understood that the detailed description and specific examples, while indicating preferred embodiments of the invention, are given by way of illustration only, since various changes and modifications within the spirit and scope of the invention will become apparent to those skilled in the art from this detailed description.

The invention claimed is:

1. A method of treating a viral infection or suppressing viral replication in a subject having a viral infection, comprising the step of administering to said subject a pharmaceutical composition comprising a pharmaceutically acceptable carrier or excipient and a therapeutically effective amount of a compound having anti-viral activity represented by the structure of formula I:

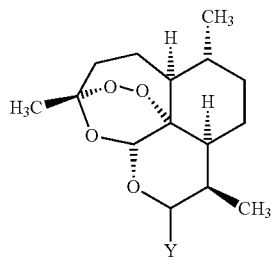

(I)

or a salt or a solvate thereof, wherein Y represents an optionally substituted morpholinosulphonyl group or a group —NR¹R²; wherein R¹ and R² together with the interjacent nitrogen atom represent an optionally substituted non-aromatic heterocyclic group selected from the group consisting of piperazinyl, morpholinyl, and thiomorpholinyl, wherein said viral infection or replication is a cytomegalovirus infection or replication, and wherein the compound inhibits cytomegalovirus infection and/or replication in said subject.

2. The method of claim 1, wherein said non-aromatic heterocyclic group is substituted.

3. The method of claim 1, wherein said viral infection or replication is a human cytomegalovirus infection or replication.

4. The method of claim 1, wherein the pharmaceutical composition is in the form selected from the group consisting of tablets, pills, capsules, pellets, granules, powders, lozenges, sachets, cachets, elixirs, suspensions, dispersions, emulsions, solutions, syrups, aerosols, ointments, soft and hard gelatin capsules, suppositories, sterile injectable solutions, and sterile packaged powders.

5. The method of claim 1, wherein the step of administering is performed via a route selected from the group consisting of oral, rectal, intramuscular, subcutaneous, intravenous, inrtaperitoneal, intranasal, intraarterial, intravesicle, intraocular, transdermal and topical.

6. The method of claim 1, further comprising co-administering said compound with at least one other anti-viral drug.

7. The method of claim 6, wherein the at least one other anti-viral drug is selected from the group consisting of ganciclovir, valganciclovir, foscarnet, cidofovir, acyclovir and valacyclovir.

8. The method of claim 6, wherein said compound and the at least one other anti-viral drug are administered in a regimen selected from the group consisting of a single combined composition, separate individual compositions administered substantially at the same time, and separate individual compositions administered under separate schedules.

9. A method of treating a viral infection or suppressing viral replication in a subject having a viral infection, comprising the step of administering to said subject a pharmaceutical composition comprising a pharmaceutically acceptable carrier or excipient and a therapeutically effective amount of a compound having anti-viral activity represented by the structure of formula VIII:

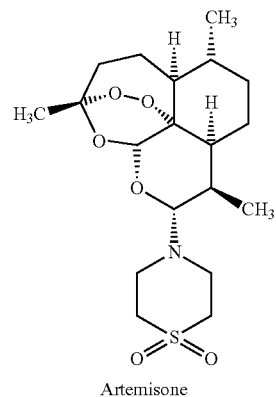

(VIII)

Artemisone or a salt or a solvate thereof, wherein said viral infection or replication is a cytomegalovirus infection or replication, and wherein the compound inhibits cytomegalovirus infection and/or replication in said subject.

10. The method of claim 9, wherein said viral infection or replication is a human cytomegalovirus infection or replication.

11. The method of claim 9, wherein the pharmaceutical composition is in the form selected from the group consisting of tablets, pills, capsules, pellets, granules, powders, lozenges, sachets, cachets, elixirs, suspensions, dispersions, emulsions, solutions, syrups, aerosols, ointments, soft and hard gelatin capsules, suppositories, sterile injectable solutions, and sterile packaged powders.

12. The method of claim 9, wherein the step of administering is performed via a route selected from the group consisting of oral, rectal, intramuscular, subcutaneous, intravenous, inrtaperitoneal, intranasal, intraarterial, intravesicle, intraocular, transdermal and topical.

13. The method of claim 9, further comprising co-administering said compound with at least one other anti-viral drug.

14. The method of claim 13, wherein the at least one other anti-viral drug is selected from the group consisting of ganciclovir, valganciclovir, foscarnet, cidofovir, acyclovir and valacyclovir.

15. The method of claim 13, wherein said compound and the at least one other anti-viral drug are administered in a regimen selected from the group consisting of a single combined composition, separate individual compositions administered substantially at the same time, and separate individual compositions administered under separate schedules.

16. The method of claim 1, wherein the subject having cytomegalovirus infection is selected from the group consisting of a newborn, a pregnant woman, and a transplant recipient.

17. The method of claim 9, wherein the subject having cytomegalovirus infection is selected from the group consisting of a newborn, a pregnant woman, and a transplant recipient.

18. A method for prevention and/or prophylaxis of a cytomegalovirus infection in an immunosuppressed subject, comprising the step of administering to said subject a pharmaceutical composition comprising a pharmaceutically acceptable carrier or excipient and a therapeutically effective amount of a compound having anti-viral activity represented by the structure of formula I:

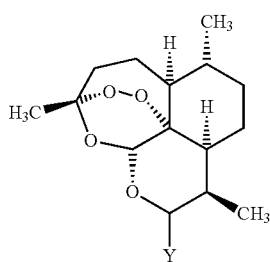

(I)

or a salt or a solvate thereof, wherein Y represents an optionally substituted morpholinosulphonyl group or a group —NR¹R²; wherein $R^1$ and $R^2$ together with the interjacent nitrogen atom represent an optionally substituted non-aromatic heterocyclic group selected from the group consisting of piperazinyl, morpholinyl, and thiomorpholinyl.

19. The method according to claim 18, wherein the subject is a transplant patient.

20. The method according to claim 19, wherein the subject has tested positive for cytomegalovirus antigen or cytomegalovirus DNA after transplantation.

21. The method according to claim 18, wherein the compound is represented by the structure of formula VIII:

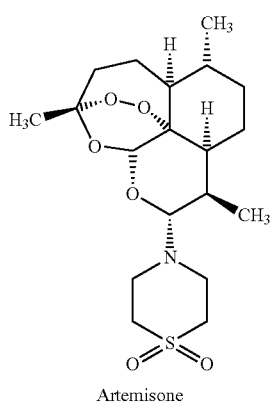

Artemisone (VIII)

or a salt or a solvate thereof.

22. A method of preventing maternal fetal transmission of a cytomegalovirus infection in a pregnant subject having a cytomegalovirus infection, comprising the step of administering to said subject a pharmaceutical composition comprising a pharmaceutically acceptable carrier or excipient and a therapeutically effective amount of a compound having anti-viral activity represented by the structure of formula I:

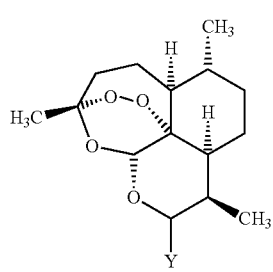

(I)

or a salt or a solvate thereof, wherein Y represents an optionally substituted morpholinosulphonyl group or a group —NR¹R²; wherein $R^1$ and $R^2$ together with the interjacent nitrogen atom represent an optionally substituted non-aromatic heterocyclic group selected from the group consisting of piperazinyl, morpholinyl, and thiomorpholinyl.

23. The method according to claim 22, wherein the compound is represented by the structure of formula VIII:

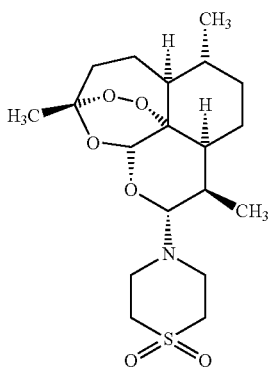

Artemisone (VIII)

or a salt or a solvate thereof.

* * * * *